US012605168B2

(12) United States Patent
Carusillo

(10) Patent No.: US 12,605,168 B2
(45) Date of Patent: Apr. 21, 2026

(54) SURGICAL HANDPIECE FOR DETERMINING BREAKTHROUGH DEPTH OF A BORE FORMED IN BONE

(71) Applicant: Stryker Corporation, Kalamazoo, MI (US)

(72) Inventor: Steve Carusillo, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 178 days.

(21) Appl. No.: 18/492,086

(22) Filed: Oct. 23, 2023

(65) Prior Publication Data

US 2024/0041475 A1 Feb. 8, 2024

Related U.S. Application Data

(63) Continuation of application No. 16/913,234, filed on Jun. 26, 2020, now Pat. No. 11,812,977, which is a continuation of application No. 15/756,825, filed as application No. PCT/US2016/049899 on Sep. 1, 2016, now Pat. No. 10,695,074.

(60) Provisional application No. 62/213,916, filed on Sep. 3, 2015.

(51) Int. Cl.
| *A61B 17/16* | (2006.01) |
| *A61B 90/00* | (2016.01) |

(52) U.S. Cl.
CPC ...... *A61B 17/1626* (2013.01); *A61B 17/1615* (2013.01); *A61B 17/1622* (2013.01); *A61B 17/1628* (2013.01); *A61B 17/1633* (2013.01); *A61B 90/03* (2016.02); *A61B 90/06* (2016.02); *A61B 17/1624* (2013.01); *A61B 2090/036* (2016.02); *A61B 2090/062* (2016.02)

(58) Field of Classification Search
CPC ...................................... A61B 17/16–17/1697
See application file for complete search history.

(56) References Cited

U.S. PATENT DOCUMENTS

| 1,831,813 | A | 11/1931 | Levedahl |
| 2,763,935 | A | 9/1956 | Whaley et al. |
| 3,804,544 | A | 4/1974 | Adams |

(Continued)

FOREIGN PATENT DOCUMENTS

| CN | 1705495 A | 12/2005 |
| CN | 1893881 A | 1/2007 |

(Continued)

OTHER PUBLICATIONS

English language abstract and machine-assisted English translation for CN 1705495 A extracted from espacenet.com database on Nov. 28, 2023, 17 pages.

(Continued)

*Primary Examiner* — Zade Coley

(74) *Attorney, Agent, or Firm* — Howard & Howard Attorneys PLLC

(57) ABSTRACT

A drill for driving a drill bit into a solid object such as bone. The drill includes a rotor with a bore that transmits rotational movement to the drill bit. The drill bit extends through the rotor bore. A probe extends forward from the drill to measure bore depth. The probe is moveably mounted to the drill so as to extend into the rotor bore. As the drill and drill bit advance forward the probe remains static. As a result of the advancement of the drill the rotor extends over the proximal end of the probe.

19 Claims, 23 Drawing Sheets

(56) References Cited

U.S. PATENT DOCUMENTS

| | | | |
|---|---|---|---|
| 3,897,166 A | 7/1975 | Adams | |
| 4,310,269 A | 1/1982 | Neu et al. | |
| 4,359,906 A | 11/1982 | Cordey | |
| 4,688,970 A | 8/1987 | Eckman | |
| 4,752,161 A | 6/1988 | Hill | |
| 5,071,293 A | 12/1991 | Wells | |
| 5,156,221 A | 10/1992 | Breitenmoser | |
| 5,257,531 A * | 11/1993 | Motosugi | B23B 49/001 |
| | | | 73/660 |
| 5,339,712 A | 8/1994 | Keyvani | |
| 5,667,509 A | 9/1997 | Westin | |
| 5,678,641 A | 10/1997 | Manschitz et al. | |
| 5,895,389 A | 4/1999 | Schenk et al. | |
| 6,033,409 A * | 3/2000 | Allotta | B25F 5/003 |
| | | | 606/80 |
| 6,096,042 A | 8/2000 | Herbert | |
| 6,106,301 A | 8/2000 | Merril | |
| 6,336,931 B1 | 1/2002 | Hsu et al. | |
| 6,391,005 B1 * | 5/2002 | Lum | A61B 5/150137 |
| | | | 604/117 |
| 6,514,258 B1 * | 2/2003 | Brown | A61C 1/084 |
| | | | 408/202 |
| 6,565,293 B2 | 5/2003 | Desmoulins | |
| 6,591,698 B1 | 7/2003 | Carlsson et al. | |
| 6,620,101 B2 | 9/2003 | Azzam et al. | |
| 6,665,948 B1 | 12/2003 | Kozin et al. | |
| 6,719,962 B2 | 4/2004 | Day et al. | |
| 6,748,273 B1 | 6/2004 | Obel et al. | |
| 6,776,562 B2 | 8/2004 | Morrison et al. | |
| 6,786,683 B2 | 9/2004 | Schaer et al. | |
| 6,863,136 B2 | 3/2005 | Bar-Cohen et al. | |
| 7,076,883 B2 | 7/2006 | Yamamoto et al. | |
| 7,111,411 B2 | 9/2006 | Knopfle et al. | |
| 7,131,974 B2 | 11/2006 | Keyer et al. | |
| 7,141,074 B2 | 11/2006 | Fanger et al. | |
| 7,163,542 B2 | 1/2007 | Ryan | |
| 7,165,336 B2 | 1/2007 | Kim | |
| 7,188,431 B2 | 3/2007 | Herrmann et al. | |
| 7,220,088 B2 | 5/2007 | Ferrari et al. | |
| 7,482,819 B2 * | 1/2009 | Wuersch | B23B 49/006 |
| | | | 408/8 |
| 7,580,743 B2 | 8/2009 | Bourlion et al. | |
| 7,636,943 B2 | 12/2009 | Gruper et al. | |
| 7,748,273 B2 | 7/2010 | Halevy-Politch et al. | |
| 7,771,133 B2 | 8/2010 | Oomura et al. | |
| 7,848,799 B2 | 12/2010 | Herndon | |
| 8,043,313 B2 | 10/2011 | Krolik et al. | |
| 8,092,457 B2 | 1/2012 | Oettinger et al. | |
| 8,241,229 B2 | 8/2012 | Herndon | |
| 8,249,696 B2 | 8/2012 | Fisher et al. | |
| 8,402,829 B2 | 3/2013 | Halevy-Politch et al. | |
| 8,419,746 B2 | 4/2013 | Bourlion et al. | |
| 8,460,297 B2 | 6/2013 | Watlington et al. | |
| 8,463,421 B2 | 6/2013 | Brett et al. | |
| 8,480,682 B2 | 7/2013 | Howlett et al. | |
| 8,486,119 B2 | 7/2013 | Bourlion | |
| 8,487,488 B2 | 7/2013 | Kuhn et al. | |
| 8,511,945 B2 * | 8/2013 | Apkarian | A61B 17/1626 |
| | | | 408/112 |
| 8,734,153 B2 | 5/2014 | Arzanpour et al. | |
| 8,821,493 B2 * | 9/2014 | Anderson | A61B 90/06 |
| | | | 606/171 |
| 8,894,654 B2 * | 11/2014 | Anderson | B25B 21/002 |
| | | | 173/176 |
| D719,594 S | 12/2014 | Leugers | |
| 8,911,448 B2 | 12/2014 | Stein | |
| 8,926,614 B2 | 1/2015 | Hsieh | |
| D722,627 S | 2/2015 | Leugers | |
| 8,970,207 B2 * | 3/2015 | Baumgartner | A61B 90/06 |
| | | | 324/207.2 |
| 8,992,535 B2 | 3/2015 | Miller | |
| D727,985 S | 4/2015 | Leugers | |
| 9,033,707 B2 | 5/2015 | Dricot | |
| D732,364 S | 6/2015 | Rinaldis et al. | |
| 9,204,885 B2 | 12/2015 | McGinley et al. | |
| 9,216,459 B2 | 12/2015 | Richt et al. | |
| 9,237,885 B2 | 1/2016 | Stein et al. | |
| D759,244 S | 6/2016 | Leugers | |
| D759,245 S | 6/2016 | Leugers | |
| 9,358,016 B2 | 6/2016 | McGinley et al. | |
| 9,370,372 B2 | 6/2016 | McGinley et al. | |
| D793,831 S | 8/2017 | Russell et al. | |
| D793,832 S | 8/2017 | Russell et al. | |
| D793,833 S | 8/2017 | Russell et al. | |
| D794,190 S | 8/2017 | Russell et al. | |
| D794,196 S | 8/2017 | Russell et al. | |
| 9,826,984 B2 | 11/2017 | McGinley et al. | |
| 9,828,157 B2 | 11/2017 | Roesler | |
| 9,999,469 B2 | 6/2018 | Roesler | |
| 10,028,801 B1 | 7/2018 | McGinley et al. | |
| 10,321,920 B2 | 6/2019 | McGinley | |
| 10,398,453 B2 | 9/2019 | McGinley et al. | |
| 10,420,625 B2 | 9/2019 | Suzuki et al. | |
| 10,695,074 B2 | 6/2020 | Carusillo | |
| 2001/0047887 A1 | 12/2001 | Wentworth et al. | |
| 2002/0058958 A1 | 5/2002 | Walen | |
| 2003/0049082 A1 | 3/2003 | Morrison et al. | |
| 2004/0059317 A1 | 3/2004 | Hermann | |
| 2004/0243145 A1 * | 12/2004 | Bobo, Sr. | A61B 17/1695 |
| | | | 606/129 |
| 2005/0116673 A1 | 6/2005 | Carl | |
| 2005/0131416 A1 | 6/2005 | Jansen et al. | |
| 2005/0171553 A1 | 8/2005 | Schwarz et al. | |
| 2006/0074405 A1 | 4/2006 | Malackowski et al. | |
| 2007/0085496 A1 | 4/2007 | Philipp et al. | |
| 2007/0090788 A1 | 4/2007 | Hansford et al. | |
| 2007/0206996 A1 | 9/2007 | Bharadwaj et al. | |
| 2009/0221922 A1 | 9/2009 | Lec et al. | |
| 2009/0245956 A1 * | 10/2009 | Apkarian | A61B 17/1695 |
| | | | 408/11 |
| 2009/0326537 A1 * | 12/2009 | Anderson | A61B 17/17 |
| | | | 606/80 |
| 2010/0034605 A1 | 2/2010 | Huckins et al. | |
| 2010/0167233 A1 | 7/2010 | Dricot | |
| 2011/0020084 A1 | 1/2011 | Brett et al. | |
| 2011/0230886 A1 | 9/2011 | Gustilo et al. | |
| 2011/0245833 A1 * | 10/2011 | Anderson | A61B 17/1628 |
| | | | 606/80 |
| 2012/0123417 A1 | 5/2012 | Smith | |
| 2012/0310247 A1 | 12/2012 | Hsieh | |
| 2013/0138106 A1 | 5/2013 | Kumar | |
| 2013/0245629 A1 | 9/2013 | Xie | |
| 2013/0261628 A1 | 10/2013 | Burley et al. | |
| 2013/0338669 A1 | 12/2013 | Brianza et al. | |
| 2014/0018810 A1 | 1/2014 | Knape et al. | |
| 2014/0046332 A1 | 2/2014 | Premanathan et al. | |
| 2014/0114316 A1 | 4/2014 | Xu et al. | |
| 2014/0148808 A1 | 5/2014 | Inkpen et al. | |
| 2014/0222003 A1 | 8/2014 | Herndon et al. | |
| 2014/0232316 A1 * | 8/2014 | Philipp | B01F 35/90 |
| | | | 318/504 |
| 2014/0262408 A1 | 9/2014 | Woodard | |
| 2014/0371752 A1 * | 12/2014 | Anderson | A61B 17/1624 |
| | | | 606/80 |
| 2015/0066030 A1 | 3/2015 | McGinley et al. | |
| 2015/0066035 A1 | 3/2015 | McGinley et al. | |
| 2015/0066036 A1 | 3/2015 | McGinley et al. | |
| 2015/0066037 A1 | 3/2015 | McGinley et al. | |
| 2015/0066038 A1 | 3/2015 | McGinley et al. | |
| 2015/0080966 A1 * | 3/2015 | Anderson | B25B 23/0064 |
| | | | 606/280 |
| 2015/0141999 A1 | 5/2015 | McGinley et al. | |
| 2015/0148805 A1 | 5/2015 | McGinley et al. | |
| 2015/0148806 A1 | 5/2015 | McGinley et al. | |
| 2016/0051265 A1 | 2/2016 | Jones et al. | |
| 2016/0120553 A1 * | 5/2016 | Xie | A61B 17/162 |
| | | | 606/80 |
| 2016/0128704 A1 | 5/2016 | McGinley et al. | |
| 2016/0244234 A1 | 8/2016 | Mayer et al. | |
| 2017/0128081 A1 | 5/2017 | McGinley | |
| 2017/0143396 A1 | 5/2017 | McGinley et al. | |
| 2017/0143440 A1 | 5/2017 | McGinley et al. | |

(56) References Cited

U.S. PATENT DOCUMENTS

| | | | |
|---|---|---|---|
| 2017/0181753 | A1 | 6/2017 | Langeland |
| 2017/0189037 | A1 | 7/2017 | McGinley et al. |
| 2018/0185034 | A1 | 7/2018 | McGinley et al. |
| 2019/0040810 | A1 | 2/2019 | Andersson et al. |
| 2020/0323543 | A1 | 10/2020 | Carusillo |

FOREIGN PATENT DOCUMENTS

| | | | |
|---|---|---|---|
| CN | 101530341 | A | 9/2009 |
| CN | 102159277 | A | 8/2011 |
| CN | 102287429 | A | 12/2011 |
| CN | 202376105 | U | 8/2012 |
| CN | 102756139 | A | 10/2012 |
| CN | 103029744 | A | 4/2013 |
| CN | 103070713 | A | 5/2013 |
| CN | 103654910 | A | 3/2014 |
| CN | 204394613 | U | 6/2015 |
| DE | 102011003828 | A1 | 8/2012 |
| DE | 102011111671 | A1 | 2/2013 |
| EP | 1330192 | A2 | 7/2003 |
| EP | 1374784 | A1 | 1/2004 |
| JP | S58164613 | U | 11/1983 |
| JP | S6110708 | A | 1/1986 |
| JP | H04226869 | A | 8/1992 |
| JP | H07299618 | A | 11/1995 |
| JP | 2005043177 | A | 2/2005 |
| JP | 2009529358 | A | 8/2009 |
| KR | 20100050763 | A | 5/2010 |
| WO | 9724991 | A1 | 7/1997 |
| WO | 9810387 | A2 | 3/1998 |
| WO | 2009158115 | A1 | 12/2009 |
| WO | 2013029582 | A1 | 3/2013 |
| WO | 2014144797 | A1 | 9/2014 |
| WO | 2015006296 | A1 | 1/2015 |
| WO | 2015014471 | A2 | 2/2015 |
| WO | 2015017681 | A2 | 2/2015 |
| WO | 2015034562 | A1 | 3/2015 |
| WO | 2015070159 | A1 | 5/2015 |
| WO | 2016036756 | A1 | 3/2016 |
| WO | 2017040783 | A1 | 3/2017 |
| WO | 2017083989 | A1 | 5/2017 |
| WO | 2017083992 | A1 | 5/2017 |
| WO | 2017139674 | A1 | 8/2017 |
| WO | 2017172949 | A1 | 10/2017 |

OTHER PUBLICATIONS

English language abstract and machine-assisted English translation for CN 102287429 A extracted from espacenet.com database on Nov. 28, 2023, 15 pages.

English language abstract and machine-assisted English translation for CN 103029744 A extracted from espacenet.com database on Nov. 28, 2023, 29 pages.

English language abstract for JPH 04-226869 A extracted from espacenet.com database on Nov. 13, 2023, 1 page.

English language abstract for JPH 07-299618 A extracted from espacenet.com database on Nov. 13, 2023, 2 pages.

English language abstract and machine-assisted English translation for WO 2015/014471 A2 extracted from espacenet.com database on Nov. 13, 2023, 8 pages.

Diaz, Inaki et al., "Bone Drilling Methodology and Tool Based on Position Measurements", Computer Methods and Programs in Biomedicine 112, 2013, pp. 284-292.

English language abstract and machine-assisted English translation for CN 101530341 extracted from espacenet.com database on Mar. 29, 2018, 11 pages.

English language abstract and machine-assisted English translation for CN 103070713 extracted from espacenet.com database on Jul. 20, 2020, 9 pages.

English language abstract and machine-assisted English translation for CN 202376105 extracted from espacenet.com database on Jul. 20, 2020, 4 pages.

English language abstract and machine-assisted English translation for CN 204394613 extracted from espacenet.com database on Mar. 29, 2018, 12 pages.

English language abstract and machine-assisted English translation for DE 10 2011 003 828 A1 extracted from espacenet.com database on Mar. 24, 2022, 6 pages.

English language abstract and machine-assisted English translation for JPS 58-164613 U extracted from espacenet.com database on Mar. 24, 2022, 3 pages.

English language abstract and machine-assisted English translation for JPS 61-10708 A extracted from espacenet.com database on Mar. 24, 2022, 5 pages.

English language abstract and machine-assisted English translation for KR 20100050763 extracted from espacenet.com database on Mar. 29, 2018, 9 pages.

English language abstract and machine-assisted English translation for WO 2013029582 extracted from espacenet.com database on Mar. 29, 2018, 18 pages.

English language abstract for EP 1330192 extracted from espacenet.com database on Mar. 29, 2018, 1 page.

English language abstract for JP 2005-043177 A extracted from espacenet.com database on Oct. 20, 2022, 2 pages.

International Search Report for Application No. PCT/US2016/049899 dated Nov. 16, 2016, 4 pages.

Machine-assisted English language abstract and machine-assisted English translation for DE 10 2011111671 extracted from espacenet.com database on Mar. 29, 2018, 28 pages.

Machine-assisted English language abstract for JP 2009-529358 A extracted from espacenet.com database on Mar. 24, 2022, 2 pages.

McGinley Orthopaedic Innovations, "Revolutionary Intellisense Drill", 2014, 4 pages.

McGinley Orthopaedics, "IntelliSense Drill Technology", 2016, 4 pages.

English language abstract for CN 1893881 A extracted from espacenet.com database on May 8, 2024, 2 pages.

English language abstract for CN 102159277 A extracted from espacenet.com database on May 8, 2024, 2 pages.

English language abstract for CN 102756139 A extracted from espacenet.com database on May 8, 2024, 1 page.

English language abstract and machine-assisted English translation for CN 103654910 A extracted from espacenet.com database on May 8, 2024, 12 pages.

* cited by examiner

SURGICAL HANDPIECE FOR DETERMINING BREAKTHROUGH DEPTH OF A BORE FORMED IN BONE

CROSS REFERENCE TO RELATED APPLICATIONS

This application is a continuation of U.S. patent application Ser. No. 16/913,234, filed on Jun. 26, 2020, which is a continuation of U.S. patent application Ser. No. 15/756,825, filed on Mar. 1, 2018, now issued U.S. Pat. No. 10,695,074, which is the national stage of International Application No. PCT/US2016/049899, filed on Sep. 1, 2016, which claims priority to and the benefit of U.S. Provisional Patent Application No. 62/213,916, filed on Sep. 3, 2015, the disclosures of which are hereby incorporated by reference in their entirety.

FIELD OF THE INVENTION

This invention relates generally to a powered surgical drill. The powered surgical drill of this invention includes a depth gauge that measures bore depth and that does not appreciably interfere with the view of the tissue into which the associated drill bit is driven.

BACKGROUND OF THE INVENTION

One type of powered surgical tool used in orthopedic surgery is the surgical drill. This type of tool includes a housing that contains a motor. A coupling assembly, also part of the drill, releasably holds a drill bit to the motor so that, upon actuation of the motor, the drill bit rotates. As implied by its name, a surgical drill drills bores in the tissue against which the drill bit is applied. One type of surgical procedure in which it is necessary to drill a bore is a trauma procedure to repair a broken bone. In this type of procedure, an elongated rod, sometimes called a nail, is used to hold the fractured sections of the bone together. To hold the nail in place, one or more bores are driven into the bone. These bores are positioned to align with complementary holes formed in the nail. A screw is inserted in each aligned bore and nail hole. The screws hold the nail in the proper position relative to the bone.

In another type of procedure, an implant known as a plate is secured to the outer surfaces of the fractured sections of a bone to hold the sections together. Screws hold the plate to the separate sections of bone. To fit a screw that holds a plate to bone it is necessary to first drill a bore to receive the screw.

As part of a procedure used to drill a screw-receiving bore in a bone, it is desirable to know the end-to-end depth of the bore. This information allows the surgeon to select size of screw that is fitted in the bore hole. If the screw is too short, the screw may not securely hold the nail into which the screw is inserted in place. If the screw is too long, the screw can extend an excessive distance out beyond the bone. If the screw extends an excessive distance beyond the bone, the exposed end of the screw can rub against the surrounding tissue. If this event occurs, the tissue can against which the screw rubs can be damaged.

Accordingly, an integral part of many bone bore-forming procedures is the measuring of the depth of the bore. Currently, this measurement is often taken with a depth gauge separate from the drill. This requires the surgeon to, after withdrawing the drill bit from the bore, insert the depth gauge into the bore. Then, based on tactile feedback, the surgeon sets the gauge so the distal end of the gauge only extends to the far opening of the bore. Once these processes are complete, the surgeon reads the gauge to determine the depth of the bore.

A disadvantage of this protocol is that after the bore is formed, the surgeon must take the time to: insert the depth gauge in the bore; position the gauge properly to ensure the bore depth is accurately measured; read the gauge to determine bore depth; and withdraw the gauge. Having to perform these sub-steps adds to the overall time it takes to perform a surgical procedure. Having to perform these sub-steps thus goes against one of the objective of modern surgical practice; the procedure should be performed as quickly as possible to both minimize the time the interior tissue is exposed to the ambient environment and therefore open to infection and to reduce the exposure of the patient to anesthesia.

To avoid having to spend this extra time measuring bore depth, surgical drills have been proposed that include built in depth gauges. This type drill typically includes a rod that is slidably mounted to the drill housing. The rod is positioned to be parallel with and spaced away from the drill bit. A head is located at the distal end of the rod. The head is positioned to seat around the drill bit. When this drill is used, the drill is positioned so that, while the rod is extended the head is place against the bone around which the bore is to be formed. As the bore is formed, the head and rod remain static. The drill moves towards the head. A sensor mounted to the drill monitors the movement of the drill relative to the rod. The measurement from the sensor of the movement of the drill is employed as the measure of the depth of the bore.

The above type of drill can form a bore in tissue and simultaneously provide a measure of bore depth. A problem with this type of drill is that the rod, which is spaced away from the drill bit by a distance of 0.5 cm or more, and the head, which can have a diameter of 0.8 cm or more, obstruct the surgeon's view of the tissue against which the drill bit is pressed. For this reason, this particular type of drill has not proven to be a popular device for forming a bore while simultaneously providing a measure of bore depth.

SUMMARY OF THE INVENTION

This invention is related to a new and useful drill capable of simultaneously drilling a bore in tissue and providing a measure of bore depth. The drill of this invention is designed so that the depth measuring components do not appreciably obstruct the field of view of the tissue against which the drill bit is applied. A further feature of this invention is that presence of the depth measuring components do not require the surgeon to appreciable enlarge the size of the incision adjacent the bone in order to accommodate the depth measuring components.

The drill of this invention includes a drill bit that extends from the drill housing. The drill also includes a depth gauge. One component of the depth gauge is an elongated probe that is slidably mounted to the housing so as to be in close proximity to the drill bit. In many versions of the invention, the probe is a tube, a cannula, that extends over the drill bit.

To facilitate the close position of the probe relative to the drill bit, the drill bit extends forward from a cannulated rotor that provides the rotational moment that rotates the drill bit. Within the bore of the rotor, there is void space dimensioned to receive the proximal portion of the probe. In this version of the invention, the drill bit is mounted to a coupling assembly attached to the proximal end of the rotor. In some versions of the invention, the rotor is the rotor internal to the motor. In other versions of invention, this rotor is separate from the motor. A gear assembly connects the rotating shaft of the motor to this rotor so that the rotation of the motor shaft results in the rotation of the rotor that turns the drill bit and that receives the proximal end of the probe.

The drill of this invention is thus designed so that the probe extends forward from the drill through the same opening in the drill from which the drill bit also extends.

The depth gauge includes a sensor that is mounted to the drill housing. The sensor generates a signal representative of the position of the distal end of the probe relative to the housing. In practice, when the drill of this invention is used, the housing moves relative to the probe. The distal end of the drill bit is at a longitudinally position relative to the housing. Therefore, the signal output by the sensor representative of housing movement is employed as a measure of bore depth.

A further feature of the drill of this invention is the drill provides a measure of bore depth even if, after the bore is formed, the drill bit continues to advance into the patient. The drill of this invention provides this measure of bore depth by monitoring a signal generated by at least one component of the drill. In one version of the invention, this end-of-bore determination is made by monitoring the sensor signal. More particularly the sensor signal is monitored to determine if the signal indicates there has been appreciable change in the depth of the drill bit. In other versions of the invention, the end-of-bore determination is made by monitoring the torque output by the motor internal to the drill that drives the drill bit or changes in drill bit speed.

Based on the signal indication that there has been a sudden change in state of the drill, the components forming the depth gauge freeze the measurement of bore depth.

BRIEF DESCRIPTION OF THE DRAWINGS

The invention is pointed out with particularity in the claims. The above and further features and advantages of this invention are understood from the following Detailed Description taken in conjunction with the accompanying drawings in which:

DETAILED DESCRIPTION

Figure 1:
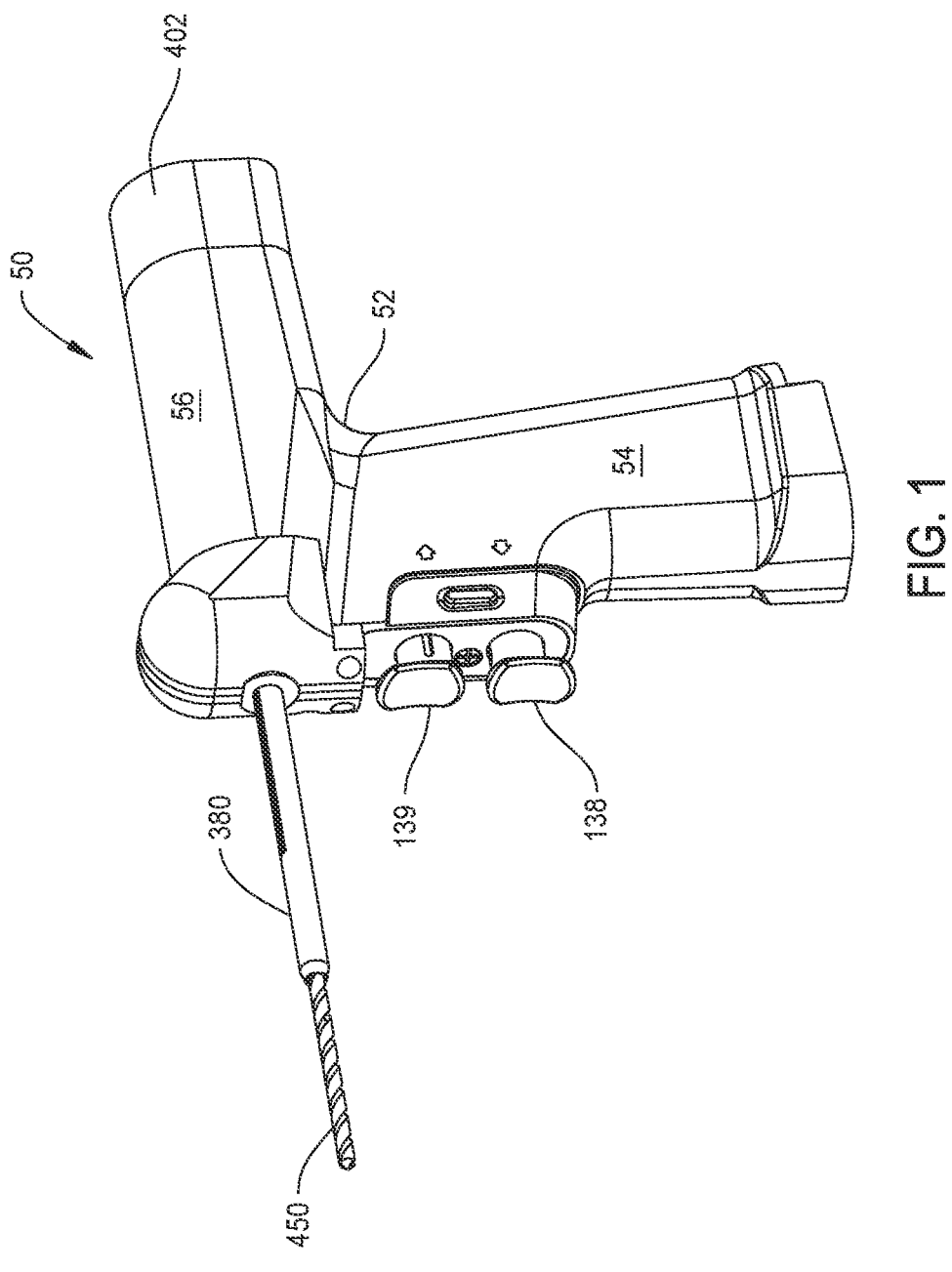
FIG. 1 is a perspective view of a surgical drill of this invention.
Figure 2:
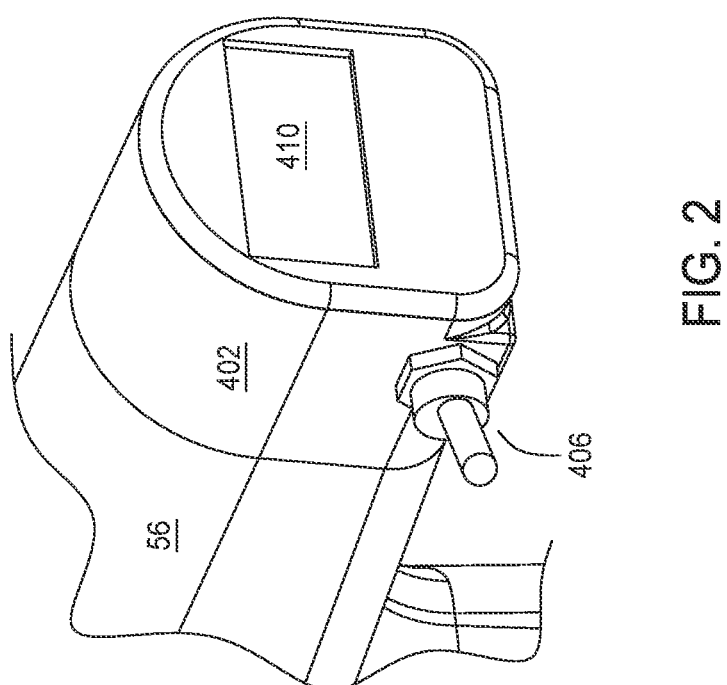
FIG. 2 is a perspective view of the proximal end of the drill.
Figure 3:
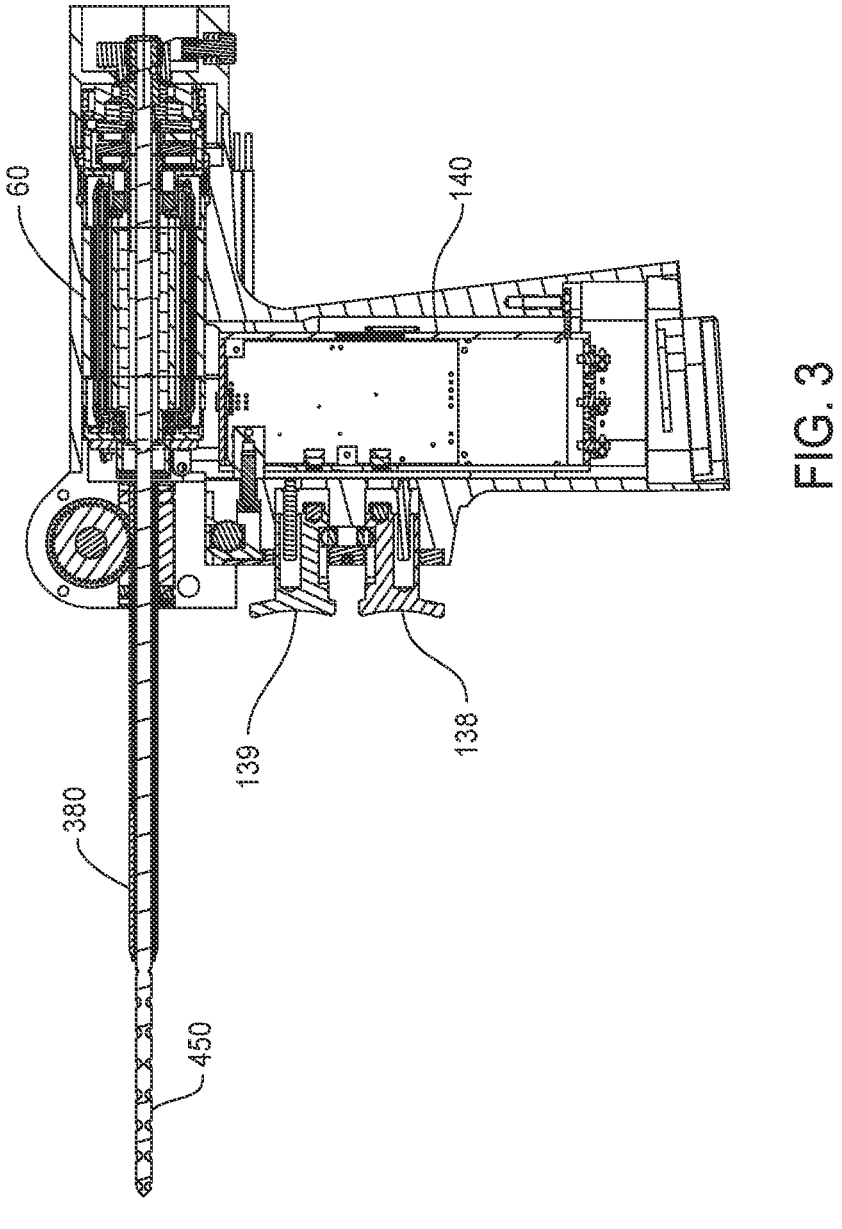
FIG. 3 is a cross-sectional view of the drill.

FIGS. 1-3 illustrate a surgical drill 50 of this invention and a drill bit 450 that extends from and is rotated by the drill 50. Drill 50 includes a housing 52. In the illustrated version of the invention, drill housing 52 is pistol shaped. The housing 52 has a grip 54. A barrel 56, also part of the housing 52, is located above and extends proximally away from the grip 54. ("Proximally" is understood to mean towards the practitioner holding the drill 50; away from the site to which the drill bit 450 is applied. "Distally" is understood to mean away from the practitioner holding the drill 50; towards the site to which the drill bit 450 is applied.) A motor 60 is disposed in the handpiece barrel 56. The drill bit 450 is connected to the motor 60 to be rotated by the motor. A display 410 is mounted to the proximal end of the barrel 56.

Power for energizing the motor 60 is typically provided by a battery (not illustrated) attached to the butt end of the handgrip 54. One such battery is disclosed in the Applicant's US Pub. No. US 2007/0090788/PCT Pub. No. WO 2007/050439, the contents of which are explicitly incorporated herein by reference. Power may also be supplied from a console over a cable that extends between the console and the drill 50. One such console is disclosed in the Applicant's US Pat. Pub. No. US 2006/0074405/PCT Pub. No. WO 2006/039331 the contents of which are explicitly incorporated herein by reference.

Manually actuatable triggers 138 and 139 extend forward from the handgrip 54 below the distal end of the barrel 56. Internal into the handgrip 54 is a control module 140. Internal to the control module 140 are sensors (not illustrated) that monitor both the state of the motor 60 and the displacement of the triggers 138 and 139. Based on the signals produced by the sensors, control module 140 selectively applies energization signals from the power source to the motor windings 85 (FIG. 7) to cause the desired actuation of the motor 60. The structure of the control module 140, including the components that regulation the actuation of the motor 60, are not part of the present invention. Further understanding of the design of the control module 140 can be obtained from US Pat. Pub. No. US 2007/0085496/PCT Pub. No. WO 2007/002180 the contents of which are explicitly incorporated herein by reference.

Surgical drill 50 of this invention also includes a probe that is located in close proximity to the drill bit 450. In the illustrated version of the invention, the probe is tube shaped, a cannula 380, that circumferentially surrounds the drill bit 450. The cannula 380 is slidably mounted to the drill housing 52. A transducer assembly 260 (FIG. 16) generates signals representative of the position of the distal end of the cannula 380 relative to the drill housing 52. Based on these signals, other components integral with the drill 50 cause data to be presented on the display 410 that indicates the depth of bore formed by the drill bit 450.

Figure 4:
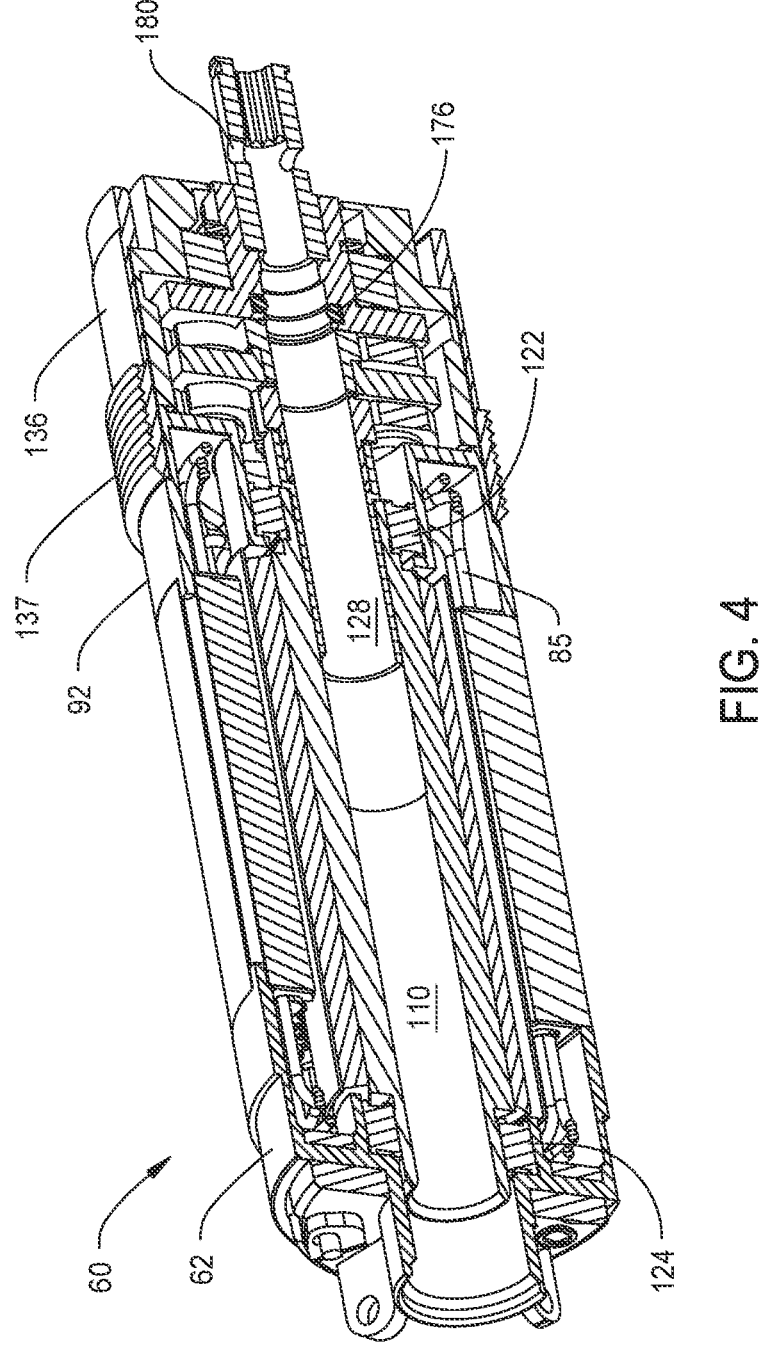
FIG. 4 is a cross sectional and partial perspective view of the motor internal to the drill.
Figures 5, 6:
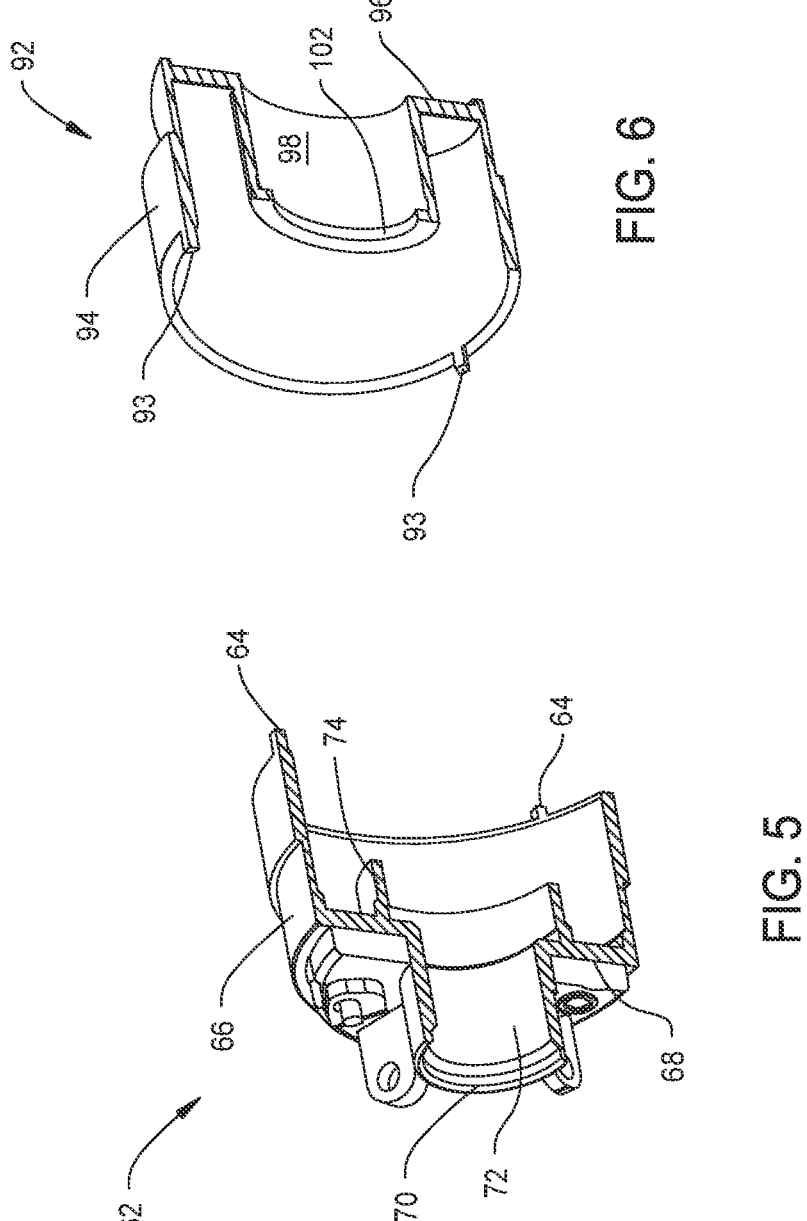
FIG. 5 is a perspective and cross sectional view of the motor front cap.
FIG. 6 is a perspective and cross sectional view of the motor back cap.

Motor 60, as seen in FIG. 4, includes a front cap 62 and a back cap 92 that is axially aligned with and spaced distally away from the front cap 62. The front cap 62, as seen in FIG. 5, includes a rim 66 that is tube like in shape. Not identified is the step between the proximal section of the rim 66 that has a large outer diameter and the distal section of the rim 66 that has a small outer diameter. Three equiangularly spaced apart feet 64, two feet seen in FIG. 5, project proximally from the proximal end of rim 66. A plate 68 extends over the distal end of the rim 66. A boss 70 extends forward from plate 68. Boss 70 is formed to define a bore 72 that extends from the distal end of the boss and opens up into the cylindrical void defined by rim 66. Front cap 62 is also formed to define a tube shaped sleeve 74. Sleeve 74 extends proximally from the proximally directed face of plate 68. The front cap 62 is formed so that the sleeve 74 is spaced radially outwardly away from opening in the plate 68 that leads into bore 72. The sleeve 74, which is located with the space defined by rim 66, is spaced radially inwardly away from the inner cylindrical wall of the rim.

The back cap 92, as seen best in FIG. 6, includes a tube like outer sleeve 94. Outer sleeve 94 has outer and inner diameters substantially equal to, respectively, the outer and inner diameters of front cap rim 66. Three equiangularly spaced apart feet 93, two feet illustrated, extend forward from the distal end of the outer sleeve 94. The back cap 92 also includes an inner sleeve 98. The inner sleeve 98 is disposed in the outer sleeve 94 and is spaced radially inwardly from the outer sleeve 94. A circularly shaped web 96, also part of back cap 92, extends between the proximal ends of sleeves 94 and 98 to connect the sleeves together. Extending distally forward from web 96, the inner sleeve 98 is shorter in length than the outer sleeve 94. A lip 102 protrudes radially inwardly from the distal end of the inner sleeve 98.

Figures 7, 8:
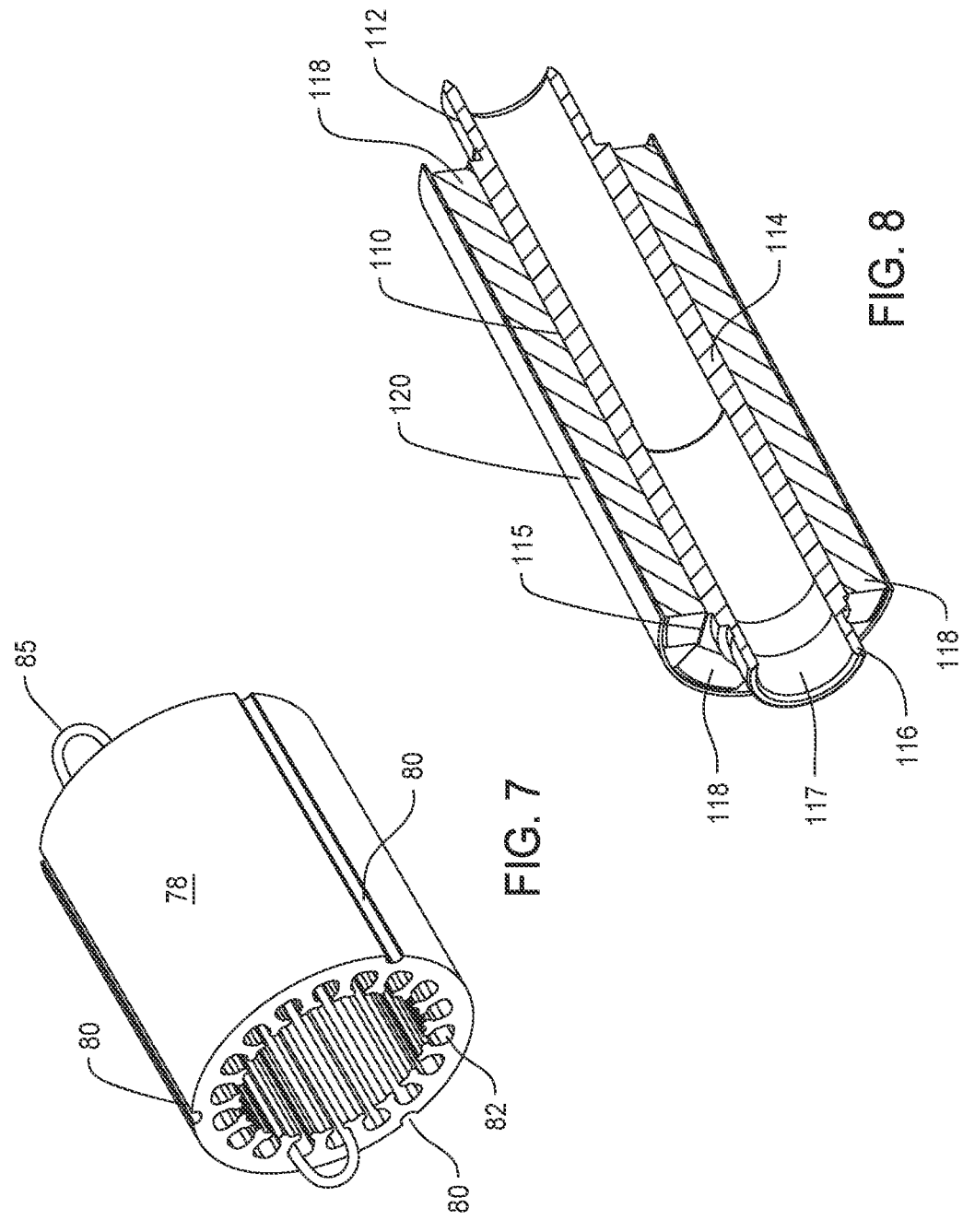
FIG. 7 is a perspective view of the lamination stack sleeve and a winding disposed in the stack.
FIG. 8 is a cross sectional and partial perspective view of the rotor internal to the motor.

A tube-shaped lamination stack 78, now described by reference to FIG. 7, is disposed between the front cap 62 and the back cap 92. The lamination stack 78 is formed from lamination steel. One such steel is nickel-iron alloy known as the Carpenter High Permeability "49" Alloy available from the Carpenter Technology Corporation of Wyomissing, Pennsylvania, United States. The outer wall of the lamination stack 78 is generally cylindrical. The outer wall of the lamination stack 78 has a diameter approximately equal to the common diameter of the rim 66 of the front 66 and outer sleeve 94 of the back cap 92. Three equiangularly spaced apart longitudinally extending grooves 80 extend inwardly from the outer surface of the lamination stack 78. When motor 60 is assembled, the proximally directed feet 64 of the front cap 62 seat in the distal ends of the grooves 80. The distally directed feet 93 that are part of the back cap 92 seat in the proximal ends of the grooves 80.

Lamination stack 78 is further formed so plural grooves 82 extend inwardly from the inner surface of the stack (one groove 82 identified). The motor windings 85, two ends of which are illustrated in FIG. 7, are seated in the grooves 82. The windings 85 extend outwardly beyond the opposed proximal and distal ends of the lamination stack 78. When motor 60 is assembled, the sections of the windings 85 that extend proximally from the lamination stack 78 extend into the annular void space between the outer and inner sleeves 94 and 98, respectively, of the back cap 92. The sections of the windings 85 that project forward of the distal end of the lamination stack 78 seat in the annular void space between rim 66 and sleeve 74 of the front cap 62.

The rotor 110 of motor 60, best seen in FIG. 8, is tube like in shape. At the proximal end, the rotor 110 has a foot 112. Foot 112 has a diameter that allows the foot to freely rotate in the circular space defined by the inner surface of lip 102 internal to the back cap 92. Forward of the foot 112, rotor 110 has a torso 114. Torso 114 is shaped so to have an outer surface that, in cross-sectional planes perpendicular to the longitudinal axis through the rotor 110, appears polygonal. The number of faces 115 torso 114 has corresponds to the number of the below discussed magnets 118 disposed over the torso. In FIG. 8, the edge of one face 115 is identified. The outer faces 115 of the torso 114 are located radially outwardly from the outer surface of foot 112. Rotor 110 is further shaped to have a head 116 that extends forward of the torso 114. Rotor head 116 has an outer diameter that is located radially inwardly from the faces 115 of the adjacent torso 114. A bore 117 extends axially through rotor 110, from the proximal end of the foot 112, to the distal end of the head 116.

Plural equiangularly spaced apart magnets 118 are disposed against the outer surface of the torso 114. Each magnet 118 is disposed over a separate one of the outer faces 115 of the torso 114. In the illustrated version of the invention, six magnets 118 are disposed over the torso 114. Three of the six magnets 118 are seen in FIG. 8. A tube shaped sleeve 120 surrounds the magnets 118. Sleeve 120 holds the magnets 118 to the rotor 110.

Bearing assemblies 122 and 124 rotatably hold the rotor 110 in the bore that extends through the lamination stack 78. (Not illustrated are the inner and outer races of the bearing assemblies 122 and 124.) The inner race of bearing assembly 122 is seated against rotor foot 112. The outer race of bearing assembly 122 is seated against the inner cylindrical surface of the inner sleeve 98 integral with the back cap 92.

The inner race of bearing assembly 124 is seated against the rotor head 116. The outer race of bearing assembly 124 is seated against the inner cylindrical surface of sleeve 74 internal to the front cap 62.

Figure 9:
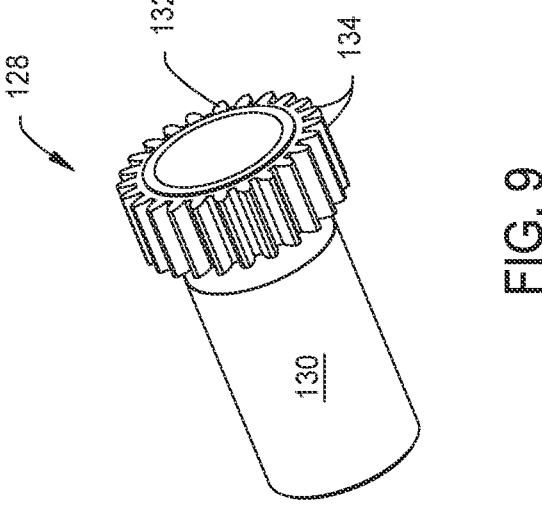
FIG. 9 is a perspective view of the output shaft attached to the motor rotor.

An output shaft 128, best seen in FIG. 9, extends proximally rearwardly from the rotor 110. Output shaft 128 has a tube like stem 130. Stem 130 is dimensioned to be compression fit in bore 117 internal to the rotor 110. A head 132 is located at the proximal end of stem 130. Head 132 has teeth 134, two teeth identified, that extend radially outwardly beyond the stem 130.

Figure 3A:
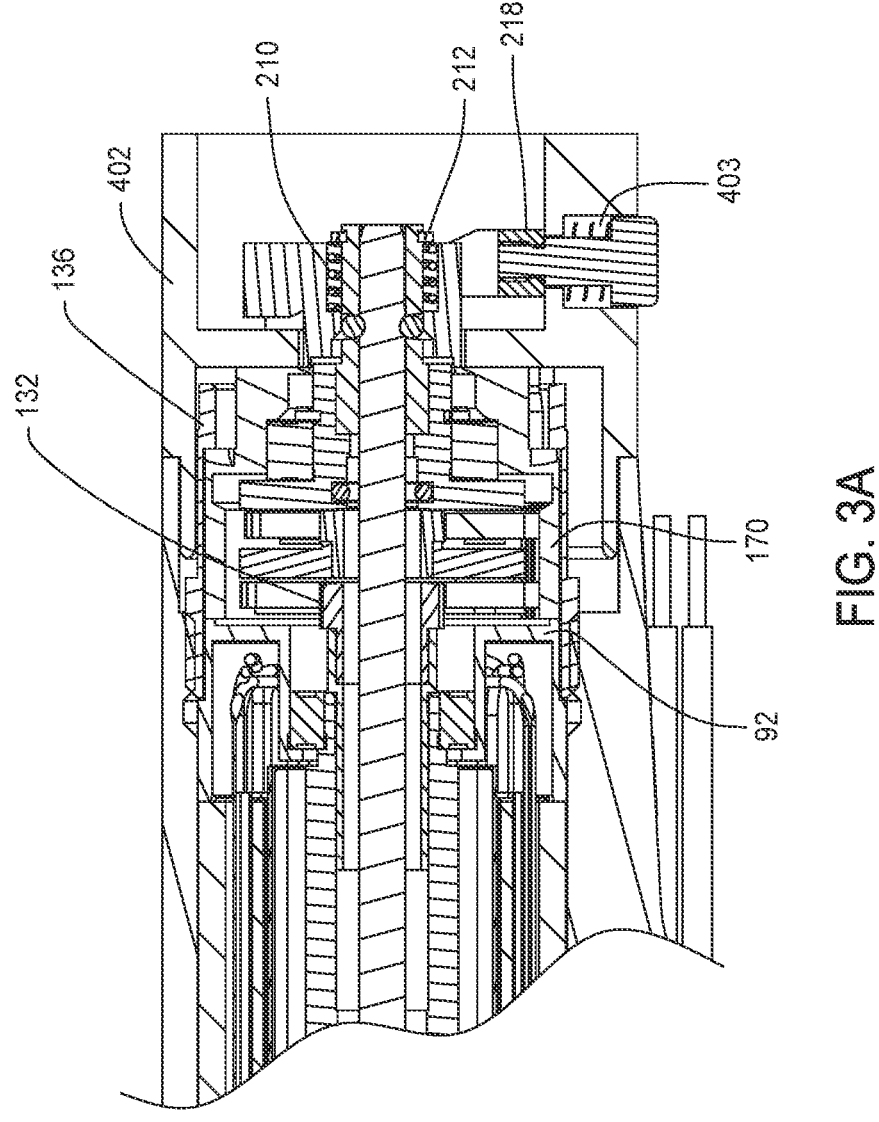
FIG. 3A is an enlarged cross sectional view of the proximal end of the barrel of the drill.

When drill 50 of this invention is assembled, it can be seen from FIG. 3A that the head 132 of the output shaft 128 is located immediately rearward of the proximal end of the motor back cap 92. A tube like motor nut 136 extends over the back cap 92 and projects rearwardly from the back cap 92. One of the outer surfaces of the motor nut 136 is formed with threading 137 seen in FIG. 4. The threading 137 of the motor nut 136 engages complementary threading on an inner surface of the barrel 56 of the housing 52. (Housing threading not illustrated). The motor nut 136 holds the motor 60 and the below described gear train 142 in the housing barrel 56.

Figure 12:
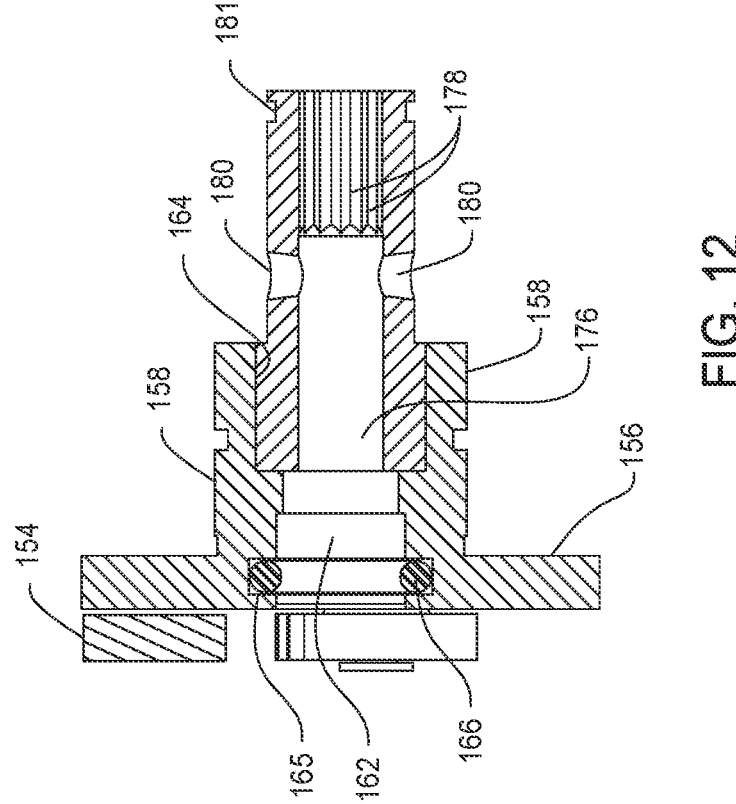
FIG. 12 is a cross section view of the proximal portion of the gear train and the drive spindle attached to the gear train.
Figures 10, 11:
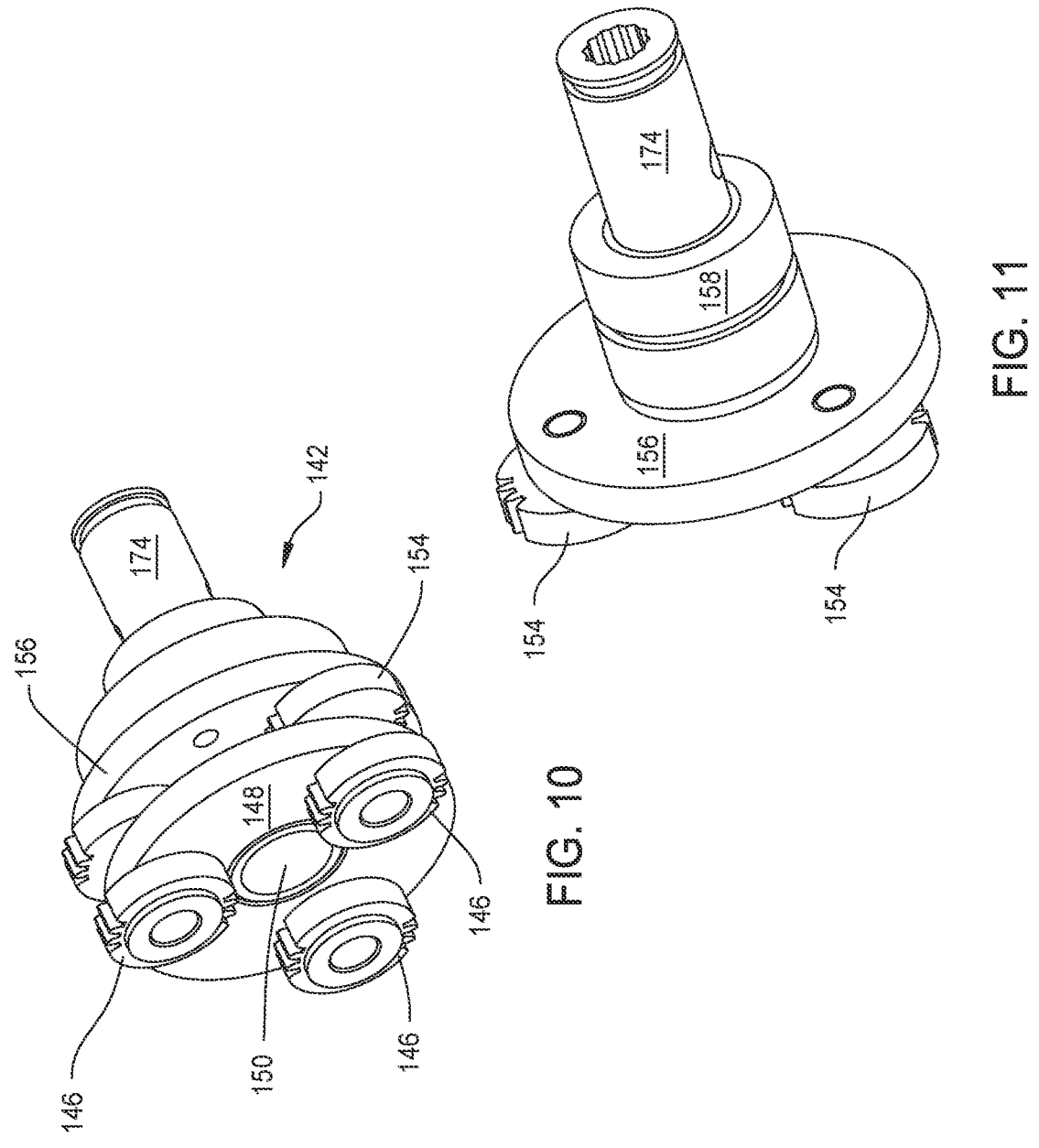
FIG. 10 is a perspective view of the gear train internal to the drill and the attached drive spindle, wherein the distally directed components of the gear train are seen.
FIG. 11 is a perspective view of a portion of the gear train internal to the drill and the attached drive spindle, wherein the proximally located components of the gear train are seen.

The gear train 142, sometimes referred to as a transmission, the components of which are seen best in FIGS. 10-12, transfers the rotational moment of the motor rotor 110 to the drill 450. In the illustrated version of the invention, the gear train 142 consists of two planetary gear assemblies. One planetary gear assembly includes a first disc shaped carrier 148. Three equiangularly spaced apart planet gears 146 are rotatably mounted to carrier 148 so as to extend forward from the distally directed face of the carrier. A bore 150 extends through the center of carrier 148. Not illustrated is the sun gear integral with carrier 148 that is located rearward of the proximally directed face of the carrier.

The second planetary gear assembly includes a second disc-shaped carrier, carrier 156. Three equiangularly spaced apart planet gears 154, two identified in FIG. 11, are rotatably mounted to carrier 156 so as to be adjacent the distally directed face of the carrier 156. A boss 158 projects rearwardly from the proximally directed face of carrier 156. Carrier 156 is further formed to have a center located bore 162. Bore 162 extends through carrier 156 and partially through boss 158. Not identified are the different sections of bore 162. Bore 162 opens into a counterbore 164 formed in boss 158. The counterbore 164, which is larger in diameter than bore 162, extends to the proximal end of boss 158.

Immediately proximal to the open end of bore 162, carrier 156 has a groove 165 that extends radially outwardly from the inner surface of the carrier that defines bore 162. An O-ring 166 is seated in the groove 165 and projects into bore 162. The O-ring 166 serves as a seal between the below described stationary cannula 602 (FIG. 33) and carrier 156.

Gear train 142 also includes a sleeve 170, identified only in FIG. 3A. Sleeve 170 abuts and extends proximally away from the back cap 92. The sleeve 170 is dimensioned to receive the planetary gear assemblies. The inner surface of the sleeve 170 is formed with teeth, (teeth not identified). Upon assembly of the gear train 140, the teeth of planet gears 146 and 154 engage the teeth integral with sleeve 170. Sleeve 170 thus functions as the single static ring gear of both planetary gear assemblies.

When drill 50 is assembled, gear train 142 is located immediately proximal to the motor 60. Head 132 of output shaft is seated between and engages planet gears 146. The output shaft head 132 thus functions as the sun gear for the first planetary gear assembly. In some versions of the invention, the gear train 132 reduces the speed of rotation so that the speed ratio of boss 158 relative to the output shaft 128 is approximately 1:10 to 1:20.

A spindle 174, also seen in FIGS. 10-12, is mounted to the boss 158 of the planetary gear assembly to rotate in unison with the boss. Spindle 174 is tube like in shape. The spindle 174 has an outer diameter that facilitates the press fitting of the spindle in the counterbore 164 internal to boss 158. The spindle 174 is formed to have a bore 176 that extends axially through the spindle between the opposed proximal and distal ends of the bore. Immediately forward of the proximal end spindle 174 is formed so that teeth 178 project inward into bore 176. The teeth 178 extend a distance equal to about one-third the overall length of the bore 176. Distal to teeth 178, bore 176 is smooth walled.

The spindle 174 is further formed to have two side bores 180. Side bores 180 are diametrically opposed to each other relative to the longitudinal axis through bore 178. The side bores 180 are located a short distance forward of the distal ends of teeth 178. Each side bore 180 extends from the outer surface of the spindle into bore 176. Each side bore 180 has a shape such that, extending radially inwardly from the outer surface of the opening, the diameter of the bore 180 decreases. A groove 181 extends inwardly and circumferentially around the outer surface of spindle 174. Groove 181 is located a short distance, less than 1 cm, forward of the proximal end of the spindle 174.

Figures 13, 14:
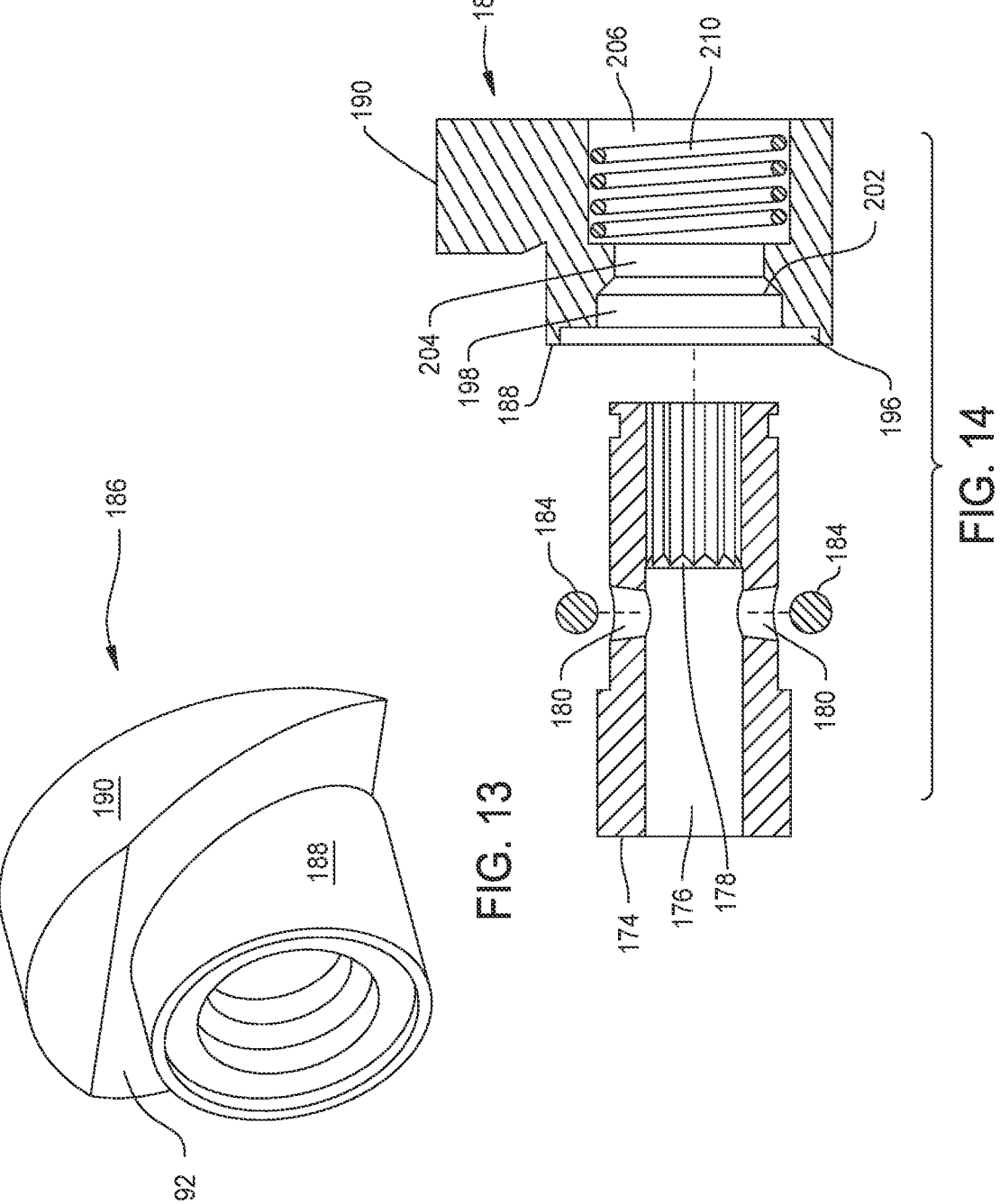
FIG. 13 is a perspective view of the lock ring internal to the drill.
FIG. 14 is a cross sectional view of the drive spindle and lock ring.

The components of a coupling assembly that releasably holds the drill bit 450 to drill 50 are now initially described by reference to FIGS. 13 and 14. The coupling assembly includes two balls 184. Each ball 184 is seated in a separate one of the side bores 180 formed in spindle 174. The components forming drill 50 are arranged so that each ball 184 can partially project through the small diameter opening of the side bore 180 in which the bore is seated. Thus, balls 184 can extend into, but not completely pass into, the main axial bore 176 formed in the spindle 174. Balls 184 are further dimensioned to project outwardly from the spindle 174.

A lock ring 186 selectively holds the balls 184 to the spindle 174 so the balls are blocked from movement out of the main axial bore 176. The lock ring 186 includes a cylindrical collar 188. Immediately proximal to the collar 188, the lock ring has a head 190. For an arc of approximately 300°, head 190 projects radially outwardly beyond the collar 188. Lock ring 186 is further formed so that the head 190 is formed with a tapered surface 192 located on the opposed sides of the collar 188. The opposed sides of tapered surface 192 start from the opposed arcuate ends of the head 190. As the sections of the tapered surface 192 extend away from these ends of head 190, tapered surface 192 angles towards the distal end of drill 50.

Lock ring 186 includes a number of contiguous bores. A bore 196 extends proximally from the distal end of collar 188. Bore 196 opens into a bore 198. Bore 198 is smaller in diameter than bore 196. A bore 202 extends proximally from the proximal end of bore 198. Bore 202 is tapered. Thus, as bore 202 extends proximally from bore 198, the diameter of bore 202 decreases. Bore 202 opens into a constant diameter bore 204. The lock ring 186 is formed so that bore 204 has a diameter equal to the adjacent smallest diameter portion of bore 202. The components forming drill 50 are further formed so that bore 204 has a diameter slightly greater than the diameter of spindle 174. The diameter of bore 204 is such that when the section of the lock ring 186 in which bore 204 is formed is disposed over the spindle side bores 180, the inner cylindrical wall of the lock ring that defines bore 204 holds balls 184 in the spindle side bores 180. More specifically, the balls 184 are held in the spindle side bores 180 so the balls extend into the main axial bore 176 of the spindle 174.

Extending proximally from bore 204, the lock ring 186 is formed to have a bore 206. Bore 206 is larger in diameter than bore 204. The lock ring 186 is formed so that bore 206 extends to the proximal of the ring head 190.

When the drill 50 is assembled, the lock ring 186 is seated over spindle 174 so that the head 190 of the ring 186 is disposed over the proximal section of the spindle. Within bore 206, a spring 210, is disposed around the spindle 174 to be located between the spindle and the inner cylindrical wall of the lock ring that defines bore 206. One end of the spring seats against a snap ring 212, seen in FIG. 3A, seated in spindle groove 181. The opposed end of the spring 210 seats against the step internal to the lock ring between bores 204 and 206. Spring 212 thus normally urges the lock ring distally forward. Lock ring 186 is normally in the position in which the inner surface of the ring that defines bore 204 is positioned around against balls 184. When lock ring 186 is in this position, the coupling assembly is in the locked position.

Figures 15, 23:
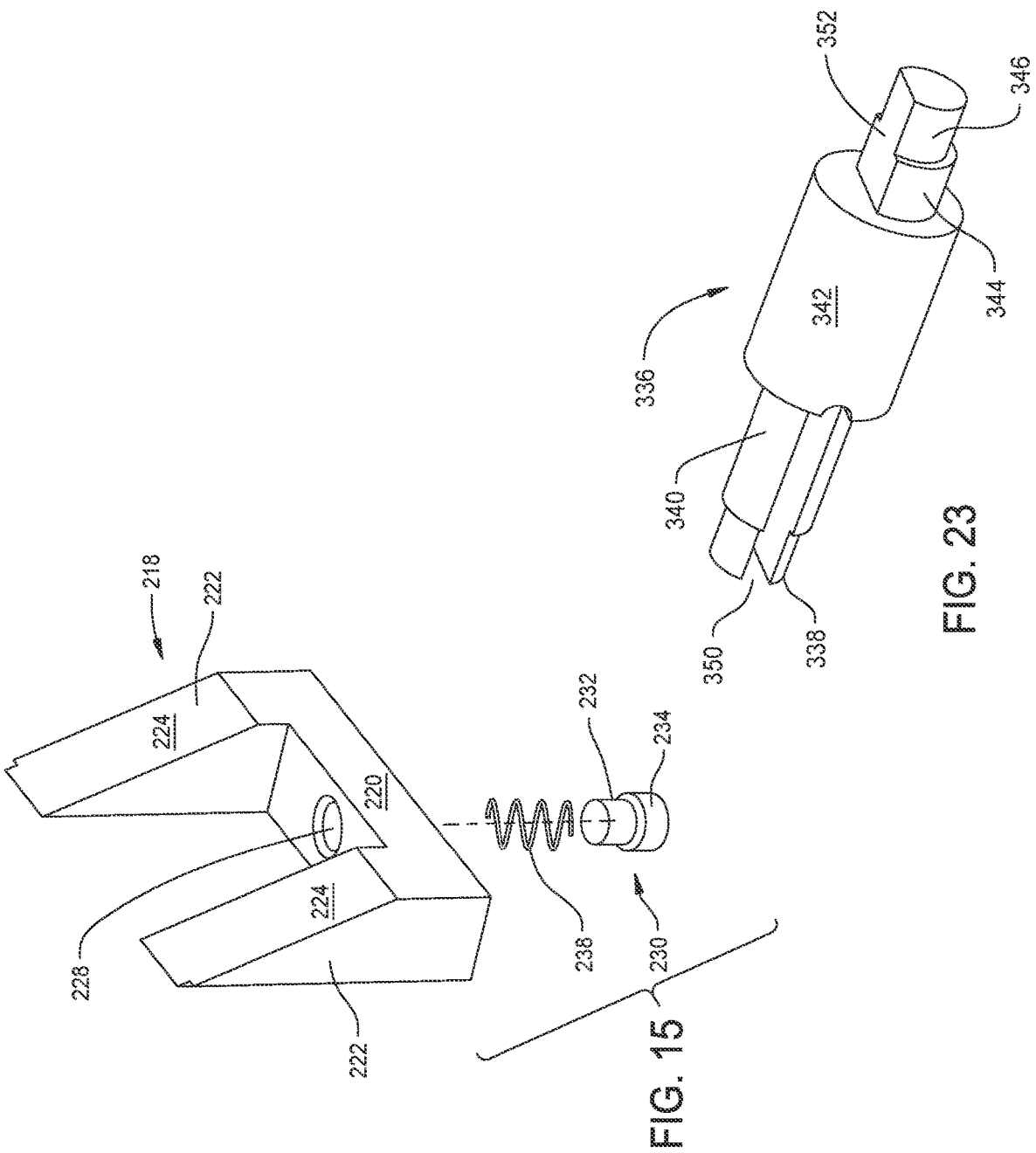
FIG. 15 is an exploded view of the lock actuator and the button used to displace the lock actuator.
FIG. 23 is a perspective view of the shaft internal to the transducer assembly.

A lock actuator 218, best seen in FIG. 15, that is moveably disposed in shell 402 moves the lock ring 186 between the locked position and a load position. The lock actuator 218 is formed with a rectangular base 220. Two parallel, spaced apart tines 222 extend outwardly from one of the major surfaces of the base. Tines 222 are spaced apart from each other so the lock ring collar 188 can seat between the tines. The lock actuator 218 is formed so the tines 222 have coplanar tapered surfaces 224. Upon assembly of drill 50, lock actuator 218 is positioned relative to the lock ring 186 so the tapered surfaces 224 of the lock ring abut the spaced apart sections of tapered surface 192 of the lock ring.

The lock actuator 218 is further formed have a bore 228. Bore 228 extends inwardly from the surface of base 220 from which the tines 222 extend. The bore 228 extends to the opposed surface of the base 220.

A release button 230 displaces the lock actuator. The release button has a stem 232 the end of which is mounted in bore 228 internal to the lock actuator 218. The stem 232 of the release button 230 extends through an opening in the shell 402 to which display 410 is mounted. The release button has a head 234 located over the end of the stem that is spaced from the actuator. The head 234 of button 230 sits in bore 403 formed in shell 402 and extends out of the shell as seen best in FIG. 3A. A spring 238 is disposed around the portion of stem 232 disposed in bore 403. One end of spring 238 seats against the annular step around the end bore 403. The opposed end of the spring 238 presses against the underside of head 234 integral with the release button 230. Spring 238 exerts a force on the release button 230 that results in the button normally holding the lock actuator 218 in a position in which the actuator base 220 is spaced from the lock ring 186. When the lock actuator 218 is in this position, the coupling assembly is in the locked state.

The transducer assembly 260, seen in FIGS. 16-19, is disposed in a pair of opposed shells that are located immediately forward of the distal end of the housing barrel 56. One shell, the right shell 262, is seen best in FIG. 20. Shell 262 includes a base 264. A semi-circular shaped arm 266 protrudes from the base. Arm 266 is dimensioned to fit in the adjacent open end of the housing barrel 56.

The right shell 262 is formed to have a number of voids. One void, void 270, extends inwardly from the face of the shell 262 that seats against the opposed left shell 286. Void 270 is circular in shape. A circular void 272 extends inwardly from the base of void 270. Void 272 has a diameter less than that of void 270. The right shell also has a notch 274. Notch 274 extends outwardly from the cylindrical wall internal to the shell that defines void 270. Another void formed in the right shell is channel 276. The right shell 262 is formed so that channel 276 is centered along a longitudinal axis that extends from arm 266 to the distal end of the shell. The channel 276 is arcuately shaped such that the base of the channel subtends an arc of approximately 150°. Channel 276 intersects void 270. Channel 276 is defined by a side wall, (not identified) immediately below void 270 that extends perpendicularly inward from the inner face of shell 262. The right shell 262 is further formed so that two semi-circular ribs 278 extend outwardly from the curved interior wall of the shell that defines channel 276. One rib 278 is located proximal to void 270. The second rib 278 is located distal to void 270.

Figures 20, 21:
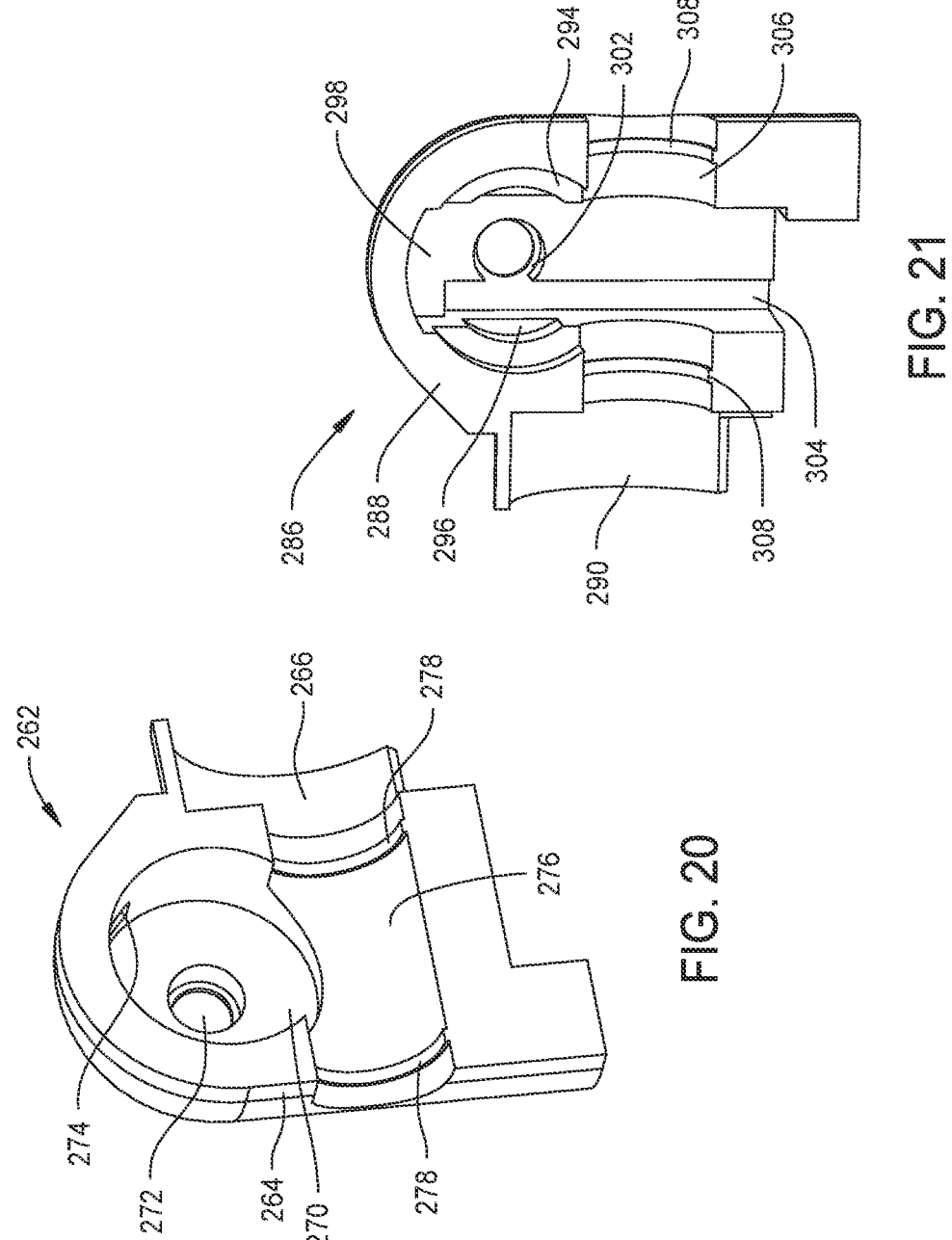
FIG. 20 is a perspective view of the interior of the right side shell of the housing for the transducer assembly.
FIG. 21 is a perspective view of the interior of the left side shell of the housing for the transducer assembly.

The left shell 286, now described with reference to FIG. 21, is the second shell in which the components forming transducer assembly 260 are housed. The left shell 286 includes a base 288. While not seen in the drawings, the outside of bases 264 and 288 of, respectively, shells 262 and 286, are essentially mirror images of each other. The left shell includes arm 290 that extends from the base 288. Arm 290 is essentially a mirror image component of the right shell arm 266.

The left shell 286 is formed to define a number of voids. One of these voids is a circular void 294 that extends inwardly from the inner face of the shell. Void 294 has the same diameter as void 270. When shells 262 are assembled together, voids 270 and 294 are contiguous. A circular void 296 extends inwardly from the base of void 294. Void 296 is smaller in diameter that void 294. The left shell 286 is also formed to have an outer channel 298 that is located inwardly of the base of void 296. Channel 298 is generally rectangular in shape. The proximal to distal width across channel 296 is less than the diameter of void 296. Channel 298 extends to the bottom of the base 288. A circular void 302 is located inwardly of the inner surface of the left shell 286 that defines the base of channel 298. The left shell is formed so that voids 294, 296 and 302 are coaxial. Void 302 has a diameter less than the diameter of void 296. Left shell 286 also has a generally rectangular inner channel 304 that is recessed relative to the outer channel 298. More particularly, the left shell 286 is formed so that void 302 and inner channel 304 have bases that are coplanar. The inner channel 304 extends inwardly from the section of the outer channel that is located closest to arm 290.

Left shell 286 also has a proximally to distally extending channel 306. Channel 306 is a mirror image of the right shell channel 276. Channel 306 intersects portions of void 294 and outer channel 298. The left shell 286 also includes two ribs 308 that project outwardly from the inner surface of the shell that define channel 306. Ribs 308 are mirror image to the ribs 278 integral with the right shell 262.

Not identified are fasteners used to hold shells 262 and 286 together or that hold the shells to the drill housing 52. When drill 50 is assembled, arms 266 and 290 extend into the open end of barrel 56. The common proximal end of contiguous channels 276 and 306 also opens into the barrel 56. A bushing 316, described by reference to FIG. 22, formed of low friction material such as bronze is disposed in the contiguous channels 276 and 306. Bushing 316 includes a proximally located foot 318 and a head 324 that is distally located and spaced forward of the foot 318. The bushing foot 318 and head 324 are each shaped like a washer that has a

Figures 16, 22:
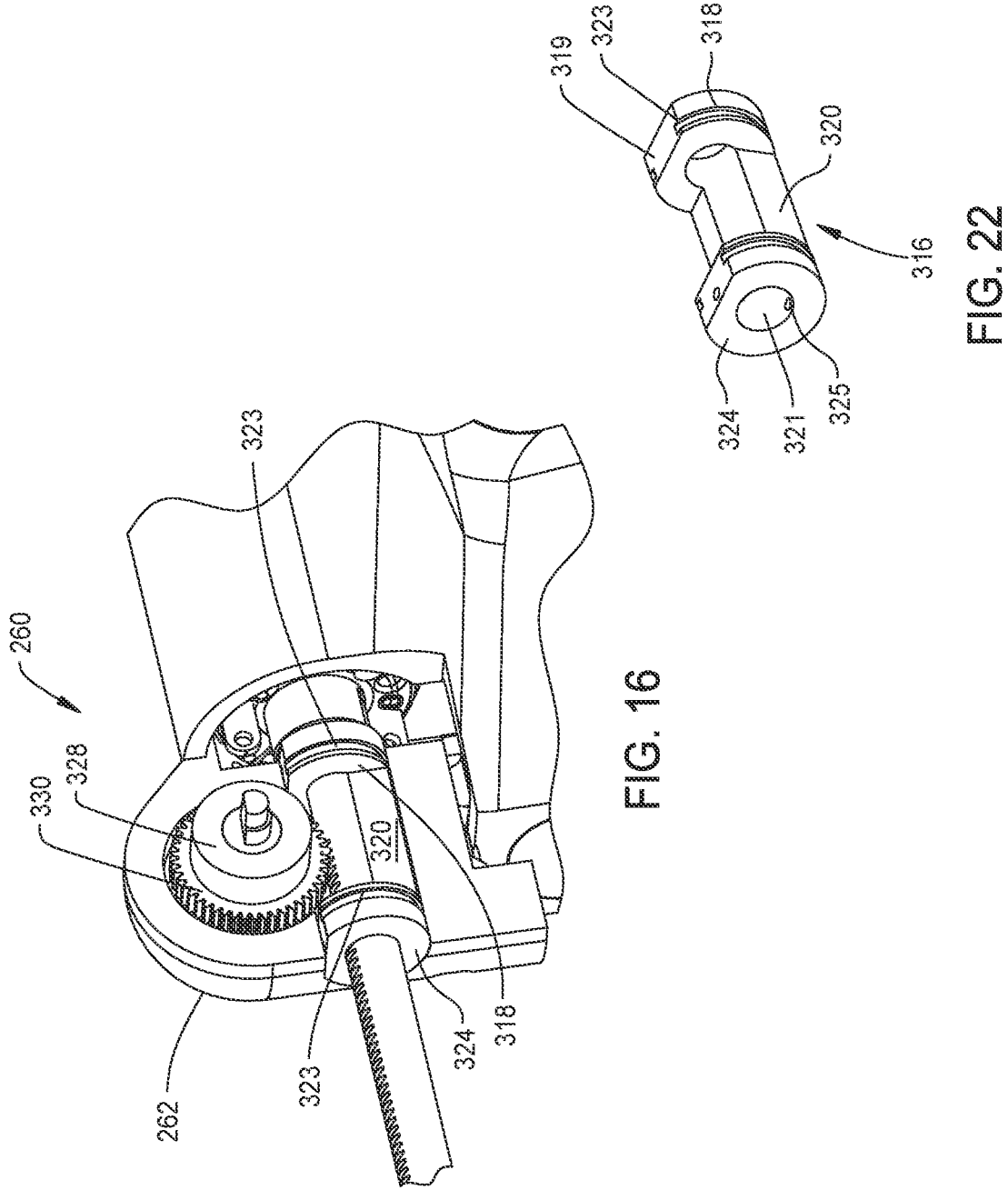
FIG. 16 is a partially disassembled view of the transducer assembly that monitors the displacement of the cannula relative to the drill body.
FIG. 22 is a perspective view of the bushing internal to the transducer assembly
Figures 17, 18:
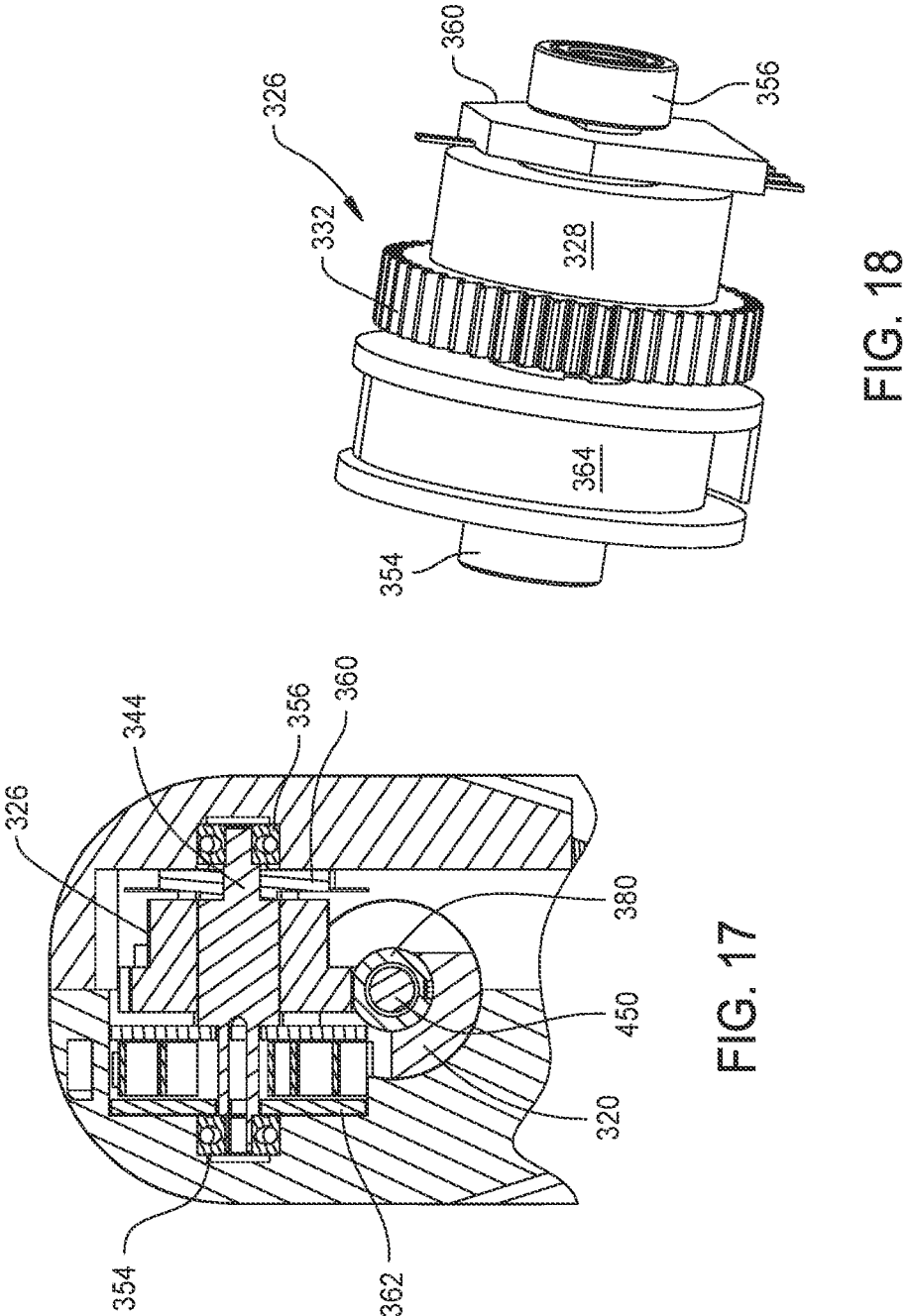
FIG. 17 is a cross sectional view of the transducer assembly.
FIG. 18 is a perspective view of the components of the transducer assembly.
Figure 19:
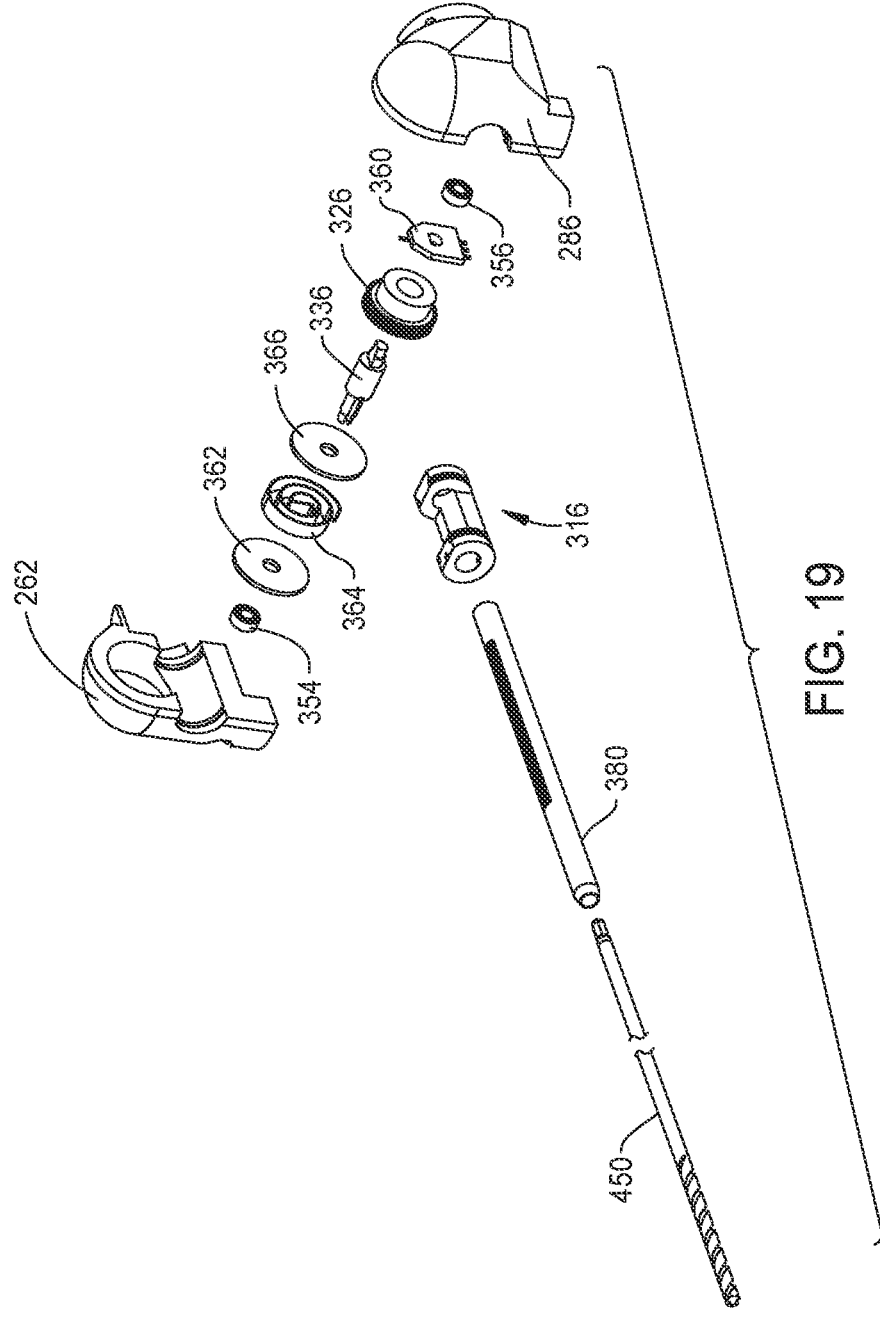
FIG. 19 is an exploded view of the interior of the transducer assembly.

11 truncated outer rim. More particularly the bushing foot 316 and head 324 are dimensioned to seat against the inner surfaces of shells 262 and 290 that, respectively, define channels 276 and 306. The bushing foot 318 and head 324 each has a flat. Only the flat 319 of the bushing foot 318 is identified. The flats abut the flat inner faces of the shells 262 and 290 that define the channels 276 and 306. This flat-against-flat abutment inhibits rotation of the bushing 316. The bushing foot 318 and head 324 each is formed with a groove 323 that extends inwardly from the outer curved surface of the component. Grooves 323 identified in FIG. 16. When the drill is assembled, ribs 278 and 308 seat in bushing grooves 323. This rib-in-groove seating serves to prevent longitudinal movement of the bushing 316 relative to the shells 262 and 286. The bushing foot 318 and head 324 each have a center-located through opening. In FIG. 22 only the opening 321 through the head 324 is identified.

A web 320, also part of bushing 316, extends between foot 318 and head 324. In cross section, in planes perpendicular to the proximal-to-distal longitudinal axis along the bush, web 320 appears arcuate in shape and subtends an arc of approximately 90°. The center openings in the foot 318 and head 324 of the bushing open into the space adjacent the web 320. A boss 325, identified only in FIG. 19, also part of bushing 320, extends inwardly from the inner surface of head 324. Boss 325 extends into opening 321.

Transducer assembly 260 includes a gear 326. Gear 326 includes a cylindrical base 328 and a coaxial cylindrical head 330. Head 330 has a diameter greater than that of the base 328. Teeth 332, one tooth identified, extend radially outwardly from the head 330. Not identified is the bore that extends axially through the gear 326.

Gear 326 seats in the voids internal to shells 262 and 286. Base 328 seats in void 296 internal to the left shell 286. The gear head 330 seats in the contiguous voids 270 and 294. The gear teeth 332 are understood to project into the contiguous channels 276 and 306. More particularly, the gear teeth are located within the channels 276 and 306 so as to be between the foot 318 and head 324 of bushing 316.

A shaft 336, seen best in FIG. 23, extends axially through gear 326. The shaft 336 includes a cylindrical foot 338. Adjacent the foot 338 the shaft includes a leg 340. Leg 340 has a diameter greater than that of foot 338. Adjacent the leg 340 the shaft has a cylindrical torso 342. The torso 342 has a diameter greater than that of the leg. The torso 342 is the portion of the shaft designed to press fit or otherwise be securely seated in the bore that extends axially through gear 326. Shaft 336 has a neck 344 that projects outwardly from the torso. Neck 344 has a shape that is partially cylindrical. The radius of curvature of the curved portion of the neck is less than the radius of the torso 342. A head 346, also part of the shaft 336, extends outwardly from the neck 344. The head 344 has a shape that is partially cylindrical. The radius of curvature of the curved surface of the head is less than radius of curvature of the adjacent curved section of the neck 344.

The shaft 336 is further formed to have a slot 350 that extends longitudinally through the foot 338 and leg 340 and, for manufacturing reasons a short distance into the torso 342. Slot 350 is centered on the common axis through the foot 338, the leg 340 and the torso 342. The shaft 336 is further formed so that the neck 344 and head 346 define a common flat 352. As will be apparent, flat 352 is present in head 346 for ease of assembly.

Two bearing assemblies 354 and 356 rotatably hold the shaft 336 and, by extension, gear 326 in the shells 262 and 286. (The races of the bearing assemblies are not identified.) Bearing assembly 354 is seated in void 272 internal to the right shell 262. Bearing assembly 354 has an inner race that extends around the shaft foot 338. The outer race of bearing assembly 354 is disposed against the cylindrical wall internal to the shell 262 that defines void 272. Bearing assembly 356 is seated in void 302 internal to the left shell 286. The outer race of the bearing assembly 356 is seated against the inner surface of the left shell 286 that defines void 302. The inner race of the bearing assembly is disposed around shaft head 346.

A potentiometer 360 is disposed in the outer channel 298 of the left shell 286. The shaft neck 344 extends through the potentiometer to displace the wiper of the potentiometer. Flat 352 abuts an adjacent flat internal to the potentiometer that rotates the wiper internal to the potentiometer. Inner channel 304 is provided to serve as the void for containing the wires that extent to the potentiometer 360. The walls that define the inner channel 304 also hold the potentiometer 360 against rotation.

Both gear 326 and the wiper of potentiometer 360 are connected to shaft 336. Therefore, the rotation of the gear 326 results in the like displacement of the potentiometer wiper.

The transducer assembly 260 also includes a spiral shaped spring 364. Spring 364 is disposed in the right shell void 270 so as to be between the base of the void and gear head 330. The outer end of spring 364 is seated in notch 274. The inner end of the spring 364 extends into the slot 350 internal to the shaft 336.

A disc 362 is disposed between the surface internal to the right shell 268 that defines the base of void 270 and the spring 364. A disc 366 is disposed between the gear head 330 and the spring 364. Not identified are the holes in discs 362 and 366 through which the shaft 336 extends. Discs 362 and 366 provide a low friction interface between spring 364 and the adjacent components of the transducer assembly 260.

Figures 24, 26:
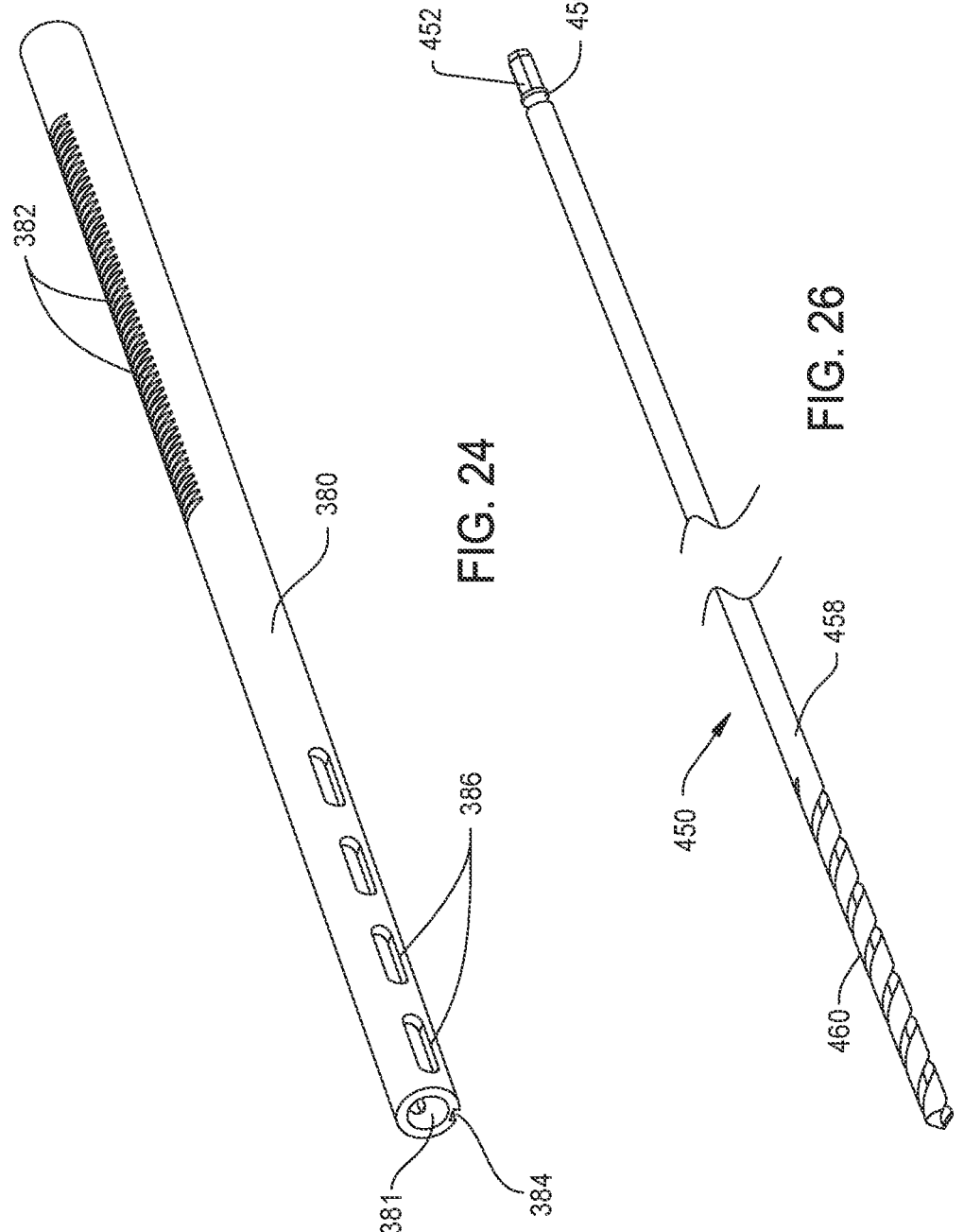
FIG. 24 is perspective view of the cannula that is part of the drill of this invention.
FIG. 26 is a perspective broken view of the drill bit used with the drill of this invention.

Cannula 380, seen best in FIG. 24, is a tube shaped structure. The cannula 380 has an outer diameter that allows the cannula to closely slip in the bore 117 that extends through the motor rotor 110. The components forming drill 50 are further arranged so that the cannula can slip through the openings forming in the foot 318 and head 324 of bushing 316. Also, the cannula can slide over the web 320 of bushing 316. Spaced forward of the proximal end of cannula 380, indentations extend arcuately across a section of the cannula so as to give the cannula teeth 382, two teeth identified. The cannula 380 is shaped so that the teeth 382 mesh with gear teeth 332. The cannula is formed so that the teeth extend a distance equal to approximately 30 to 50% of the overall length of the cannula.

A lumen 381 extends axially through the cannula. In many versions of the invention the wall thickness of the cannula between the outer surface of the cannula and the inner lumen-defining surface is 2 mm or less. In more preferred versions of the invention, this wall thickness is 1 mm or less. While not illustrated, in some versions of the invention, the distal end of the cannula is formed with a taper. This taper is such that at the most distal end of the cannula the wall thickness of the cannula is even less than the thickness of the wall proximal to this distal end.

The cannula 380 is also formed so as to have a groove 384 that extends longitudinally along the cannula. Groove 384 is shown extending into the cannula from the surface of the cannula opposite the surface in which teeth 382 are formed. Cannula 380 also is formed with a number of oval through openings 386, two openings identified. The through openings 386 are located forward of teeth 382. Openings 386 extend to the lumen 381 that extends axially through the cannula When the drill 50 of this invention is actuated, the though openings 386 function as ports through which the drilled out material is discharged from the cannula 380.

Cannula 380 is slidably mounted in the bushing 316. The cannula 380 extends through the bushing head 324 and the bushing foot 318. The cannula extends distally forward out of the through opening 321 in the bushing head 324. The specific section of the cannula mounted in the bushing is the section of the cannula on which teeth 382 are formed. The teeth 382 mesh with gear teeth 332. When the cannula 380 is mounted to the drill, the boss 325 that protrudes outwardly from the bushing web 320 seats in the groove 384 integral with the cannula. This boss-in-groove arrangement allows the cannula 380 to engage in proximal-to-distal longitudinal motion relative the rest of the drill 50 while inhibiting rotation of the cannula relative to the rest of the drill.

It should also be understood that spring 364 exerts a torque on shaft 336 that causes the shaft, and by extension gear 326, to rotate. The torque urges the shaft to rotate in the clockwise direction when viewed from the perspective of FIG. 16. The rotation of gear 326 causes the movement of the cannula. More particularly, the cannula is displaced distally forward, away from the drill housing 52. The movement of the cannula stops when the gear teeth 332 abut the teeth free portion of the cannula proximal to the cannula teeth 382. This abutment of the gear teeth against the outer surface of the cannula stops further rotation of the gear 326.

Display 410 is contained in shell 402 seen best in FIG. 2. The shell 402 is mounted to the proximal end of barrel 56. The display 410 is mounted to the shell so as to face proximally from the proximal end of the shell. Shell 402, display 410 like the other components of the drill of this invention are constructed out of components able to withstand the rigors of process used to sterilize the drill so the drill can be used in surgery. Typically, the drill 50 is constructed to be able to withstand exposure to an autoclave sterilization process. In an autoclave sterilization process, the drill is placed in an atmosphere saturated with steam (water vapor) at a temperature of 125° C. and a pressure of 2 bar.

Figure 25:
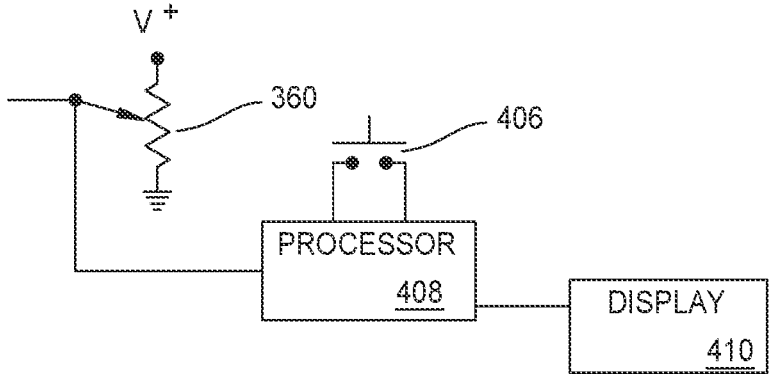
FIG. 25 is a block and partial schematic diagram of some of the signal processing components of the drill.

FIG. 25 depicts the basic electrical components of drill 50 that, based on position of the cannula 380, provide an indication of the depth of the bore formed by the drill bit 450. Not identified are the voltage regulating components that ensure the drive signals of the appropriate potentials are supplied to the bore depth displaying components. The components that provide the information about bore depth include the potentiometer 360. A voltage is applied to one end of the potentiometer 360. The opposed end of the potentiometer 360 is tied to ground. The voltage present at the wiper of the potentiometer is applied to a signal processor 408. Also shown attached to the signal processor 408 is a zeroing switch 406. In the drawings switch 406 is shown mounted to the display shell 402.

The signal processor 408 includes a number of components that are not illustrated. These components include a memory. Instructions and data needed by the drill 50 to generate the indications of bore depth are contained in the memory. The signal processor 408 also includes a clock or a timer, the purpose of which will become apparent below.

Based on changes in the voltage present between the wiper of the potentiometer 360 and one terminal of the potentiometer and the signal from the zeroing switch 406, signal processor 408 generates data representative of the depth of the bore formed by the drill bit 450. Signals representative of the bore depth are applied to the display 410.

The features of drill bit 450 are now described by reference to FIG. 26. The drill bit includes an elongated shaft 458. The components of this invention are arranged so that drill bit shaft 458 has a diameter that is approximately 0.02 to 0.25 mm less than the diameter of cannula lumen 381. The relative dimensioning of these two components allows the drill bit 450 both freely rotate and move longitudinally within the cannula 380. At the proximal end of shaft 458 the cannula has a foot 452. Foot 452, in cross sectional planes perpendicular to the proximal-to-distal longitudinal axis through drill bit 450, is polygonal in shape. More particularly, the foot 452 is shaped so the corner sections between adjacent sides can fit between the teeth 178 of the drive spindle 174. This face-against-teeth arrangement facilitates the transfer of torque from the drive spindle 174 to the drill bit 450.

Forward of foot 452 a groove 456 is formed in shaft 458. Groove 456 extends inwardly from the outer surface of the shaft and circumferentially around the shaft. Drill bit 450 is formed so that groove 456 has an arcuate shape. More particularly, the drill bit 450 is formed so that groove 450 can receive balls 184.

The distal end of drill bit 450 is formed with flutes 460, one flute identified. The flutes 460 are designed to drill out the tissue, typically bone, in which the drill 50 is used to form a bore. The geometry of the flute 460, including the geometry of the distal end of the drill bit 450 is not part of the present invention.

Preparation of drill 50 of this invention for use often starts with the releasable attachment of the drill bit 450 to the drill. To perform this process, button 230 is pressed inwardly. This results in the movement of the lock actuator 218 laterally, along a plane perpendicular to the longitudinal axis through the drill barrel 56. The tapered surfaces 224 move against the adjacent tapered surface 192 of the lock ring 186. The force imposed by the lock actuator 218 against the lock ring 186 is sufficient to overcome the force spring 210 places on the lock ring to hold the lock ring in the locked position. The lock ring 186 is thus urged proximally. As a result of this movement of the lock ring 186, the section of the ring that defines bore 204 moves proximally away from the spindle side bores 180 and balls 184. The balls 184 are able to move out of spindle main bore 176. The coupling assembly is in the load state.

During this process of coupling the drill bit 450 to the drill it may be necessary to push the cannula 380 proximally so the cannula retracts into the drill barrel 56. Finger force is sufficient to overcome the force spring 364 places on the cannula so as to hold the cannula in the extended position.

Once the coupling assembly is in the load state, the drill bit 450 is inserted into the drill 50. The drill bit 450 is inserted through the cannula 380. Once the proximal portion of the drill bit 450 moves proximally past the rotor, this portion of the drill bit moves through the bores 150 and 142 internal to gear train 142 and into the drive spindle 174. As a result of this positioning of the drill bit 450, the corners of the drill bit foot 452 seat between the teeth 178 of the drive spindle 174. Once the drill bit 450 is so secured, the finger force applied to button 230 is released. Spring 238 returns the release button 230 and the lock actuator 218 to the locked state. Spring 210 then urges the lock ring 186 back to the locked state. As a result of the movement of the lock ring 186, the tapered surface of the ring that defines bore 202 is urged against the balls. This lock ring-against balls abutment urges the balls into the fully seated position in bores 180. Once the lock ring 186 fully returns to the locked position, balls 184 are constrained from outward movement by the surface of the lock ring that defines bore 204. The balls 184 are thus locked in the groove 456 internal to the drill bit 450. The seating of balls 184 in groove 456 holds the drill bit to the drive spindle 174.

Once the drill bit 450 is locked to the drive spindle 174, force used to hold the cannula 380 in the retracted position is released. The torque produced by spring 364 causes the rotation of gear 326 that returns the cannula to the extended position. When the cannula 380 is so positioned, the distal end of the cannula is located a short distance forward of the distal end of the drill bit 450. This distance is typically less than 1 cm.

It should also be understood that when drill bit 450 is mounted to the housing 52, the drill bit extends out from the housing through the same opening, opening 321 in bushing head 324, from which the cannula 380 extends distally forward.

If necessary, the drill 50 is connected to a power supply such as a battery or a power console.

To set the drill 50 for use, the drill is first positioned so the distal end of the cannula 380 abuts the surface of the bone around which the bore is to be formed. If the bore is to be formed below a surgical implant such as a plate, after the implant is positioned, the drill is positioned so the cannula abuts the exposed surface of the implant. The implant is formed with an opening through which the drill bit is pressed in order to form the bore. As a result of this initial positioning of the drill 50, the cannula 380 is blocked from further advancement.

While the cannula 380 is blocked from advancement, it is still possible to advance the drill bit 450 and, by extension, drill 50 distally forward. This is because spring 364 does not exert enough force to inhibit counterclockwise rotation of gear 326. Thus, once the cannula is positioned, the positioning of the drill continues with the advancing of the drill bit 450 through cannula until the distal end of the bit strikes the surface of the tissue through which the bore is to be formed.

In this and the subsequent step of actually drilling the bone visually it appears as if the cannula is retracting into the drill 50. In actuality, the cannula 380 is static. The drill 50 advances over the cannula 380.

The abutment of the drill bit 450 against the target tissue stops the further advancement of the drill 50. At this time, the drill is set to form the desired bore in the tissue. At this time the zeroing switch 406 is depressed, step 482 of FIG. 27A. In response to receiving the signal that the zeroing button is depressed, processor 408 stores the voltage present at the wiper of potentiometer 360 as the zero-state voltage for the procedure.

To advance the drill bit 450, the surgeon depresses the appropriate trigger 138 or 139. For the purposes of this description, it is assumed that, when trigger 138 is depressed, the control module 140 causes drive signals to be applied to the motor that cause the forward rotation of the drill bit, the rotation of the bit that drives the bit into the bone, (step not illustrated).

As the drill bit is advanced into the bone, step 484, the drill housing 50 and components inside the housing advance with the drill bit. Cannula 380, it is recalled, is blocked from advancing by the continued abutment of the cannula against the tissue or implant surrounding the tissue in which the bore is being formed. As a result of the movement of drill housing 52, gear 326 continues to be rotated by the movement of the gear over the cannula 380. The rotation of the gear results in the like displacement of the wiper of potentiometer 360. This results in a change in the voltage output of the potentiometer relative to the zero state voltage. Step 486 represents the measurement of the voltage of the wiper of the potentiometer as well as the time the measurement is made. As part of step 486 the time the voltage measurement is made is also recorded. These time data are based on the time or clock data from the timer or clock internal to the drill 50. Step 488 is the calculation by the signal processor of the difference between these two voltages. This second voltage is referred to as the present state voltage.

Based the difference between the present state voltage and the zero state voltage, processor 408, in a step 490 determines the current depth of the bore being formed by drill bit 450. In some versions of the invention, this determination is made by using this voltage difference as the input variable into an algorithm. The output value of this algorithm is the current depth of the bore. Alternatively, the determination of current bore depth in step 490 is made by reference to a set of look up tables. In these tables, the input value is the voltage difference, the output value is bore depth.

It should be understood that the actual value calculated in step 490 is the measure of the circumferential distance gear 326 has advanced over the static cannula 380. This distance corresponds to the distance the drill bit 450 has advanced beyond the distal end of the cannula after the zero button was depressed. As discussed below, this distance is generally, but not always, the depth of the bore in the tissue against which the drill bit 450 is applied.

As part of step 490 the signal processor records data indicating the time each determination of bore depth is made. These time data are based on the time the voltage measurement was made.

Step 492 is the processor presenting on the display 410 the current measurement of bore depth.

As drill 50 advances, cannula 380 appears to retract into and beyond the shells 262 and 282 that contain the transducer assembly 260. The proximal section of the cannula retracts into rotor bore 117. Often cannula 380 is provided with a component that limits the extent to which the drill 50 is allowed to advance over the cannula. This is to prevent the rapidly spinning output shaft 128 from pressing against the static cannula 380. In some versions of the invention, to prevent this component abutment a static ring (not illustrated) is disposed over and rigidly mounted to the cannula. The ring is positioned so that, once the drill 50 advances a certain distance of the cannula the front face of the drill, actually the front face of bushing head 324 abuts this ring. This drill-against-ring abutment prevents the drill from advancing to a position in which the output shaft 128 presses against the cannula 380.

Typically, drill 50 is designed so that drill can advance over the cannula at least 1 cm, and more typically at least 5 cm and more preferably at least 10 cm. In most versions of the invention, drill 50 is designed so that the drill can advance over the cannula a distance at least equal to 0.5 cm more than the depth of the deepest bore the drill is intended to form.

In a step 494 the processor 408 determines if the current bore depth is greater than a previously stored deepest bore depth. If the evaluation of step 494 tests positive, the processor considers the drill 50 to be in a state in which the drill bit 450 is advancing. In a step 496 the processor resets the value of the deepest bore depth to the just calculated current bore depth.

Another step executed if the evaluation of step 494 tests positive is the determination of a breakthrough depth, step 498. The breakthrough depth is the depth of the bore at the moment the drill bit has broken through the bone. The breakthrough depth is thus the depth of the fully formed bore in the bone. In some versions of the invention, one variable used to determine breakthrough depth is the time the deepest bore depth was reached. In these versions of the invention, breakthrough depth is the deepest bore depth at a fixed time prior to when the drill bit was at the deepest bore depth.

Figure 28:
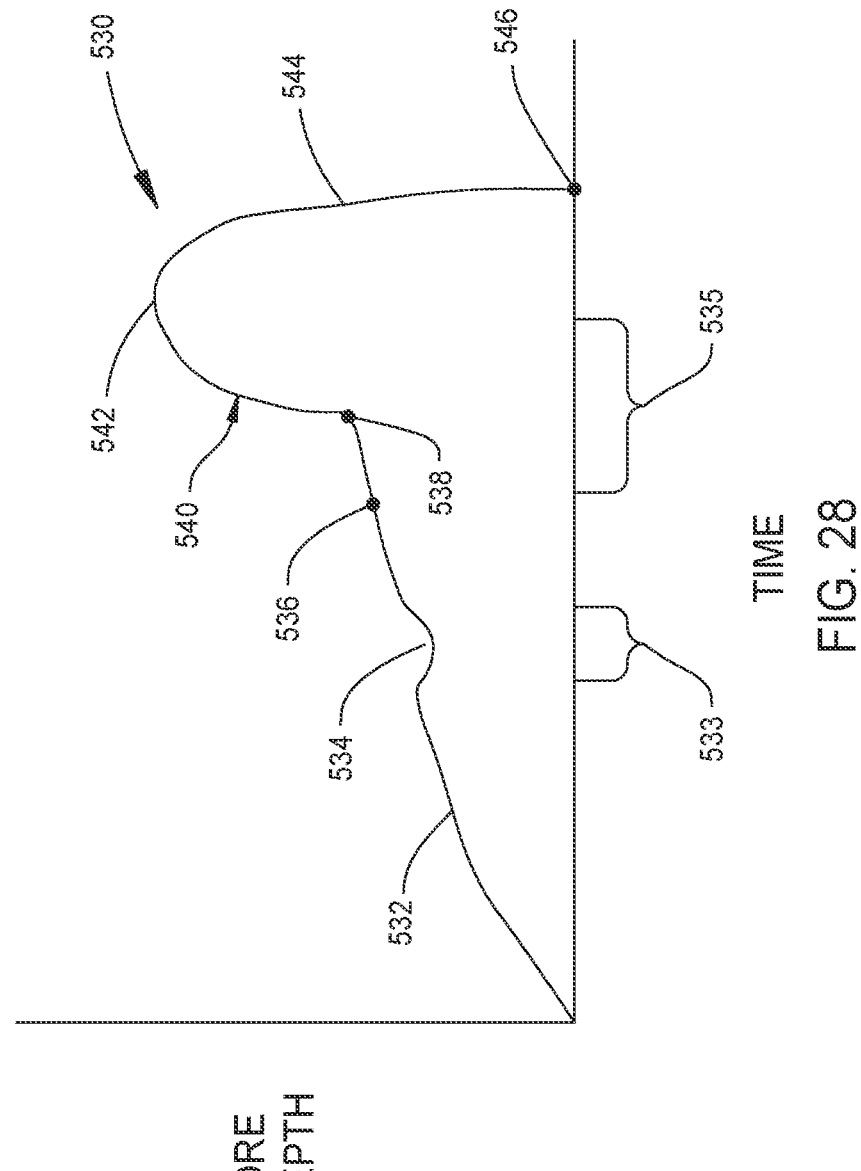
FIG. 28 is a plot of bore depth over time.

The logic behind this relationship is explained by reference to plot 530 of FIG. 28. Plot 530 represents the depth of the bore as measured by the transducer assembly over time. Section 532 of the plot represents that, as the drill bit 450 is advanced through bone, the depth of the bore over time advances at a relatively slow speed. Indentation 534 in section 532 represents that while the bit 450 is being advanced through the bone, there may be instances in which the current depth of the drill bit may be momentarily less than the bore depth. This can occur if the surgeon momentarily retracts and then resets the drill bit 450. During time period 533, after the bit is retracted until the drill bit tip again engages bone, the evaluation of step 494 tests negative.

Point 538 represents the bore depth and time at which the drill bit 450 breaks through the bone. At this time, the surgeon is still applying an axial force on the drill to advance the bit 450. Accordingly, once breakthrough occurs, the drill bit continues to advance for a short period of time. Soft tissue places less resistance on the advancement of the bit than bone. Accordingly, the advancement of bit 450 during this time period is at a speed higher than the speed at which the advancement previously occurred. This high speed advancement of the bit is represented by section 540 of plot 530. Point 542 represents the bore depth and time at which the surgeon stops advancing the drill bit. This depth is referred to as the final penetration depth. This depth is the deepest bore depth value set in the last execution of step 496.

Section 544 of plot 530 represents the complete withdrawal of the drill bit 450 from the patient. Point 546 represents that, as a result of the withdrawal of the drill bit and the retraction of the drill 50 from over the cannula 380, the processor 408 calculates the bore depth as being back at a zero depth state. It should be understood that in this withdrawal process, the surgeon typically actuates the drill bit. Often the surgeon performs this step by reverse driving the drill bit 450. In the described version of the invention, the motor 60 is run in verse by depressing trigger 139.

In one version of the invention, the determination of step 498 is based on the start time of a time frame the end of which is the time at point 542 the surgeon starts the final retraction of the drill 450. This time frame is represented by bracket 535. The start time of this time frame is represented by point 536 on the bore depth plot 530. This start time of the time frame is prior to when the breakthrough occurred, point, 538. However, the margin of error between the bur depth at the beginning of this time frame, point 536 on plot 530, and the bur depth at point 538 is typically within an acceptable range of accuracy for providing a measure of bore depth at drill bit break through.

Accordingly, as the drill bit 450 continues to advance through tissue, processor 408 continues to execute step 498. In each execution of step 498, the breakthrough depth is determined by first assigning the time at which the deepest bore depth was measured as the end time for time frame. Based on this end time, a fixed time value, the time value of the time frame, is subtracted from the end time to determine the start time. Then the bore depth at the start time for this time frame is assigned the value of the breakthrough depth. It should be understood that as long as the bore is advancing through the bone, the breakthrough bore depths determined in the plural executions of step 498 represent neither the breakthrough bore depth nor the actual depth of the bore in the bone. Only the depth determination made during the last execution of step 498, which is based on when the drill bit 450 reached the final penetration depth, represents the actual depth of the bone at break through.

The loop back from step 498 to step 486 represents that the measurement of bore depth, the display of current bore depth, the determination of whether or not the measured depth is the deepest bore depth and the calculation of a breakthrough depth occur repeatedly while the drill bit 450 is advanced through bone.

If the evaluation of step 494 tests negative, then the surgeon either has momentarily retracted the drill bit 450 or completed the process of drilling the bore. In either situation, steps 494-498 are not executed.

Instead, a step 504 is executed. In step 504 the processor evaluates whether or not based on the current measurement of bore depth measurement the drill bit indicates the drill bit has been retracted to a zero depth relative to the surface of the bone.

If the evaluation of step 504 is negative, the processor 408 considers the drill to be in a state in which the drill bit has been momentarily retracted, the period 536 of indentation 534, or the drill bit is being subjected to complete retraction, the period of section 544 of plot 530. In either case, the drill bit 450 is still in bone. The processor 408 loops back to step 486.

If the evaluation of step 504 tests positive, then the drill bit 450 is fully retracted from the bone. Processor 408 interprets the drill 50 being in this state as an indication that the bore was completely formed in the bone. Accordingly, in a step 506, the processor presents on the display the last calculated breakthrough depth as the measured depth of the bore in the bone.

Drill 50 of this invention thus provides data that accurately represents the depth of the bore the drill is used to form and provides these data without appreciably interfering with the view of the drill bit or the tissue surrounding the drill bit.

Figure 29:
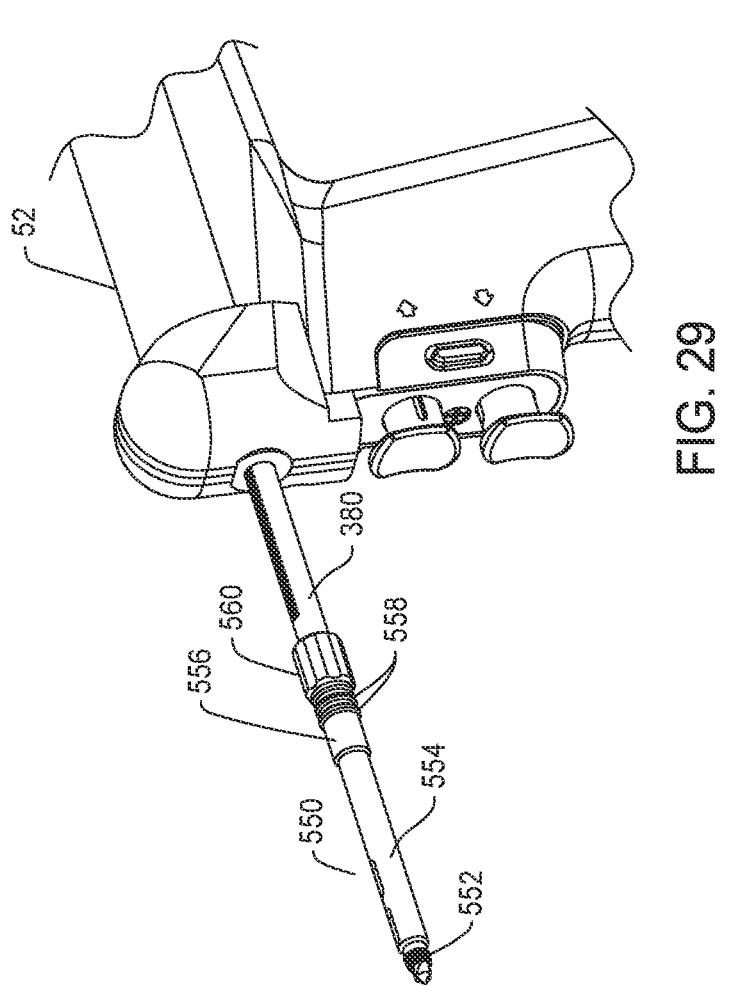
FIG. 29 is a perspective view of how a drill guide may be fitted over a drill bit.

FIG. 29 depicts how the drill 50 of this invention may be used with a drill guide 550. The drill guide 550 is used when the drill 450 is used to form bores designed to receive screws used to hold a locking style plate to the outer surface of section of bone. This type of plate is used to hold fractured sections of bone together. The locking plate is formed with small 1 through openings designed to receive the screws. The through openings are provided with threading designed to hold the screws fitted in the openings to the plate.

Figure 30:
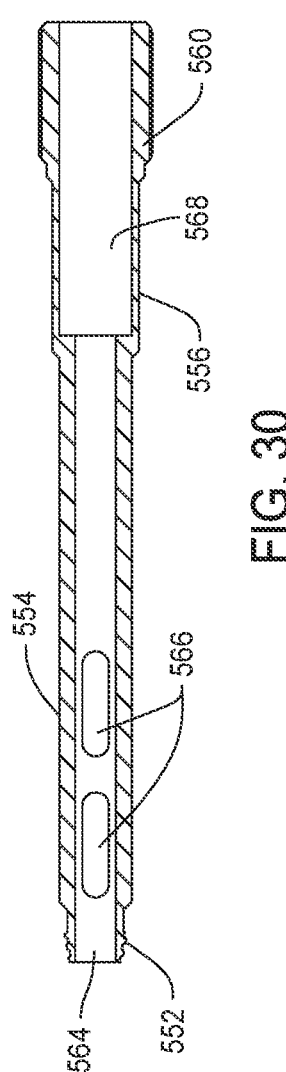
FIG. 30 is a cross sectional view of the drill guide of FIG. 29.

Drill guide 550, seen in FIGS. 29 and 30, is generally cylindrical is shape. A foot 552 forms the most distal section of the drill guide 550. The outer surface of the foot 552 is formed with threading (not identified). The foot threading is designed to engage with the threading in the plate openings. This allows the drill guide 550 to be temporarily secured in each of the plate openings. Proximal to the foot 552 the drill guide has a trunk 554. Trunk 554 has an outer diameter greater than that of the foot 552. A neck 556 extends rearward from the proximal end of the trunk 554. Forward of the neck 556, drill guide 550 has a head 560. The head 560 is largest diameter section of the drill guide 550.

A distal bore 564 extends through the foot 552 and trunk 554 and a short distance into the neck 556. Distal bore 564, like the cannula lumen 381 is dimensioned to receive the drill bit 450 so the drill bit can rotate in the bore 564. The distal bore 564 opens into a proximal bore 568. The drill guide 550 is shaped so that proximal bore 568 has a diameter greater than that of distal bore 564. More specifically, the proximal bore 568 has a diameter that allows the cannula 380 to closely slip fit in the bore 568. The proximal bore 568 extends through the neck 556 and head 560 to the proximal end of the head 560 which is the proximal end of the drill guide 550.

Drill guide 550 is further formed so that proximal to the foot a number of oval shaped openings 566 extend through the trunk 554 into the distal bore 564. Openings 566 serve the same function as openings 386 internal to the cannula 380.

A drill 50 with drill guide 550 is used by initially configuring the drill as if the drill is to be used without the drill guide. The foot 552 of the drill guide 550 is screwed into one of the bore holes of the plate adjacent which the bore is to be formed. Once the plate is properly positioned, drill bit 450 is inserted into first bore 568 and then bore 564 of the drill guide 550.

As this process proceeds, the cannula 380 eventually abuts the step internal the drill guide between the bores 564 and 568. This abutment of the cannula 380 stops the simultaneous advancement of the cannula with the drill bit 450. As the drill bit and drill continue to advance, the advancement of the drill cause the drill to move over the cannula 380. Gear 326 rotates as the gear advances over the cannula 380.

Figure 27A:
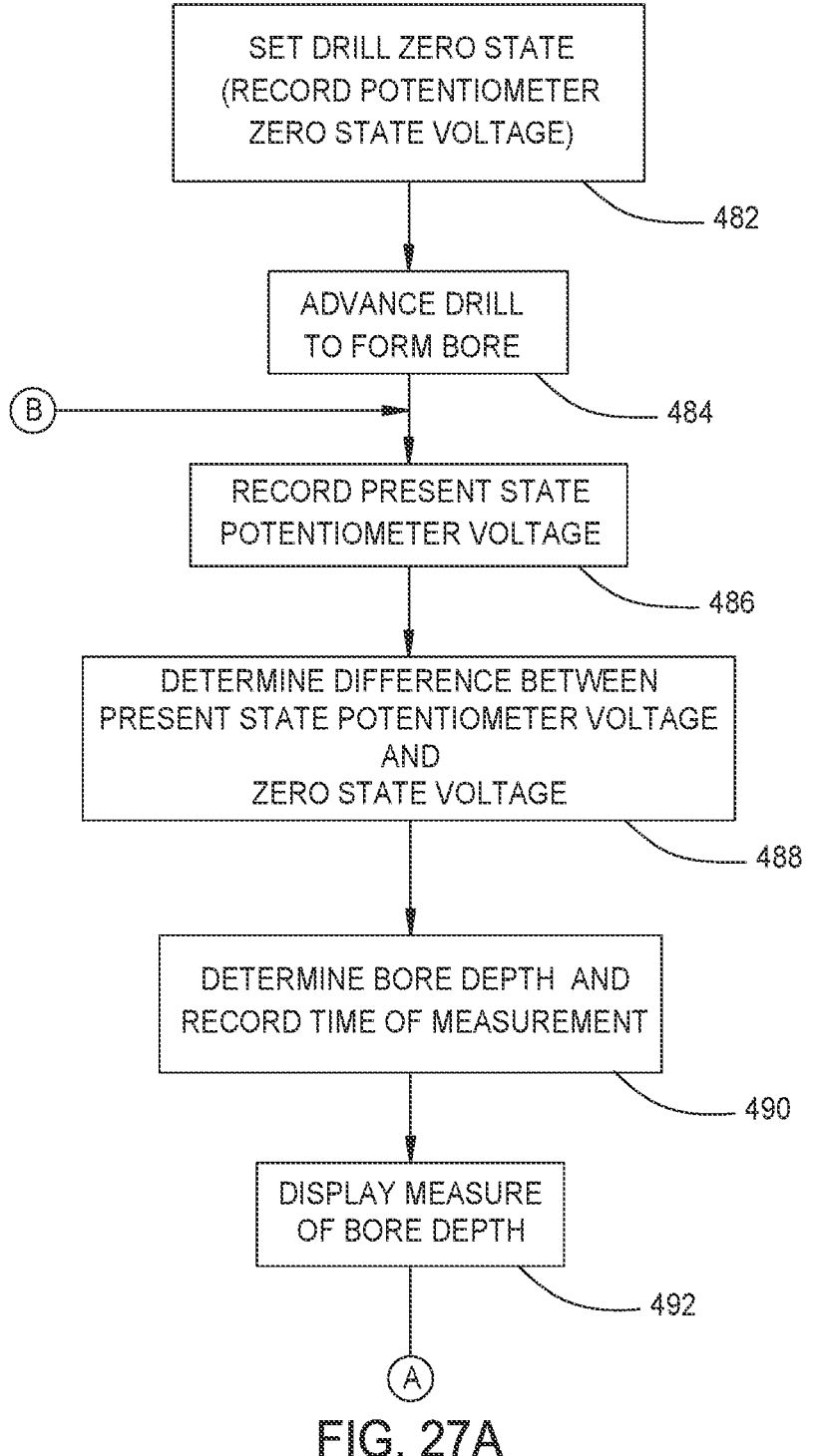
FIGS. 27A and 27B form a flow chart of the processing steps performed by the electrical components to provide an indication bore depth.
Figure 27B:
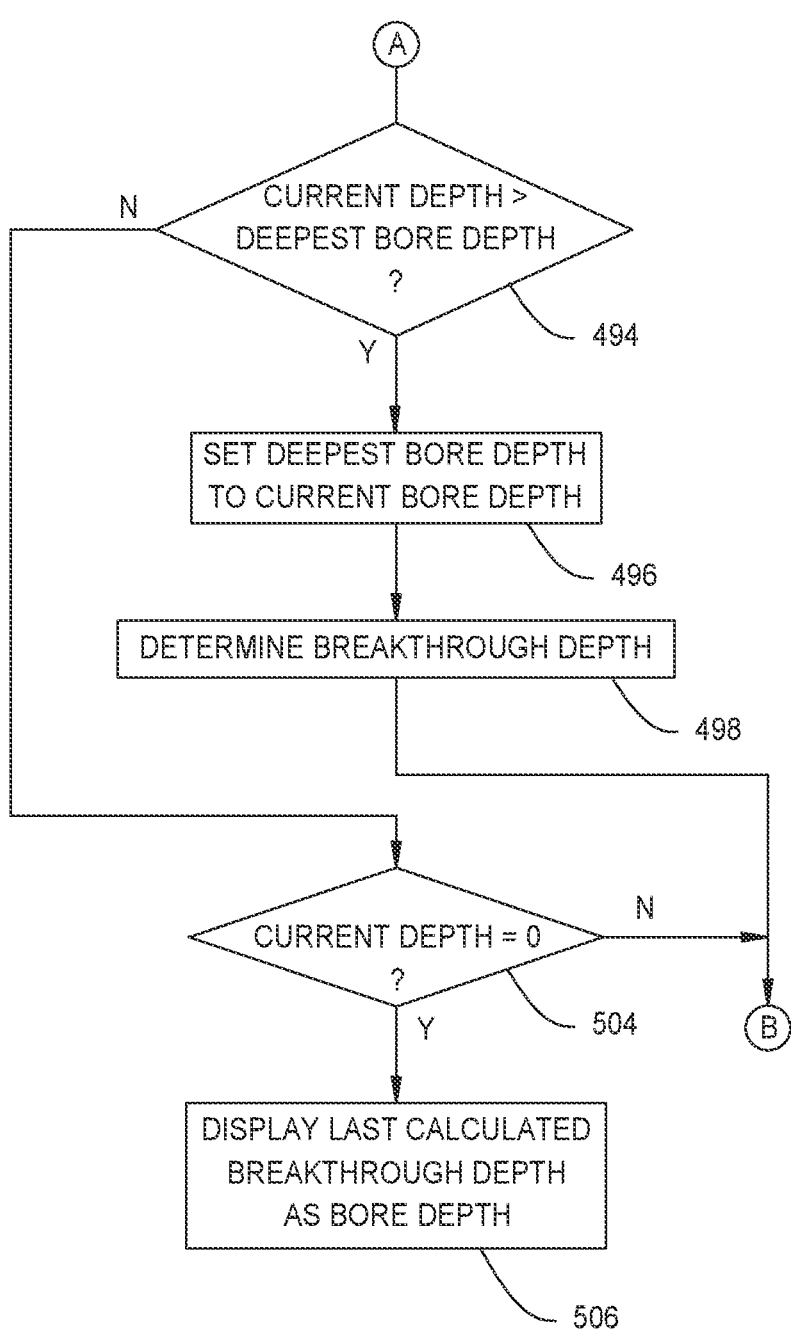

Eventually, the drill bit 450 abuts the bone to which the drill bit is to be applied. This bit-against-bone abutment stops further advancement of the drill bit and the drill 50. At this time, the drill 50 is set to form the bore in the bone. The process described with respect to FIGS. 27A and 27B is performed to both form the bore and simultaneously provide a measure of bore depth. During this use of the drill 50, it should be understood that as the drill and drill bit 450 are advanced, the cannula is held static by the continued abutment of the cannula against the step internal to the drill guide. Accordingly, in step 482 the zeroing of the cannula position is performed when the drill is in a state in which the cannula has abutted the step internal to the drill guide and the drill bit has first abutted the underlying bone. In steps 488 and 490 the calculated difference in potentiometer voltage again represents the distance the drill 50 has advanced toward the distal end of the cannula. This distance again corresponds to the depth of the bore the drill bit has formed in the bone.

By providing drill guide 550, one can use drill 50 of this invention to precisely orient the drill bit relative to the plate adjacent which the bore is to be formed. This ensures the resultant bore will have the correct orientation relative to the screw thread of the plate.

Figure 31:
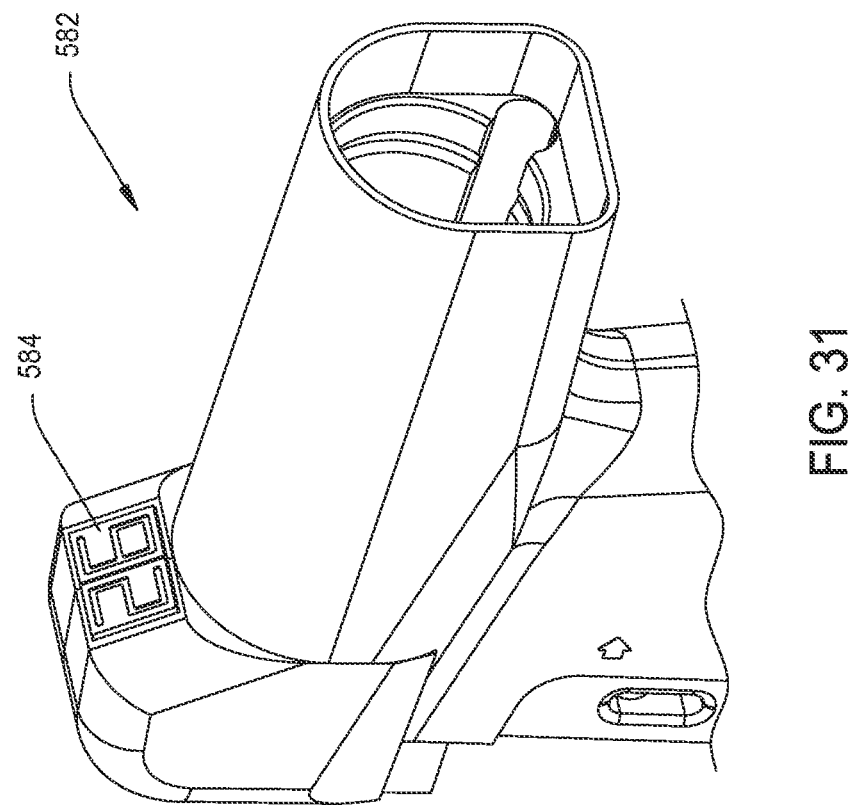
FIG. 31 is a perspective view of a portion of an alternative drill housing of this invention.

FIG. 31 depicts an alternative housing 582 for the drill of the invention. In this version of the invention, display 584 is mounted to the portion of the housing that contains the transducer assembly.

Figures 32, 33:
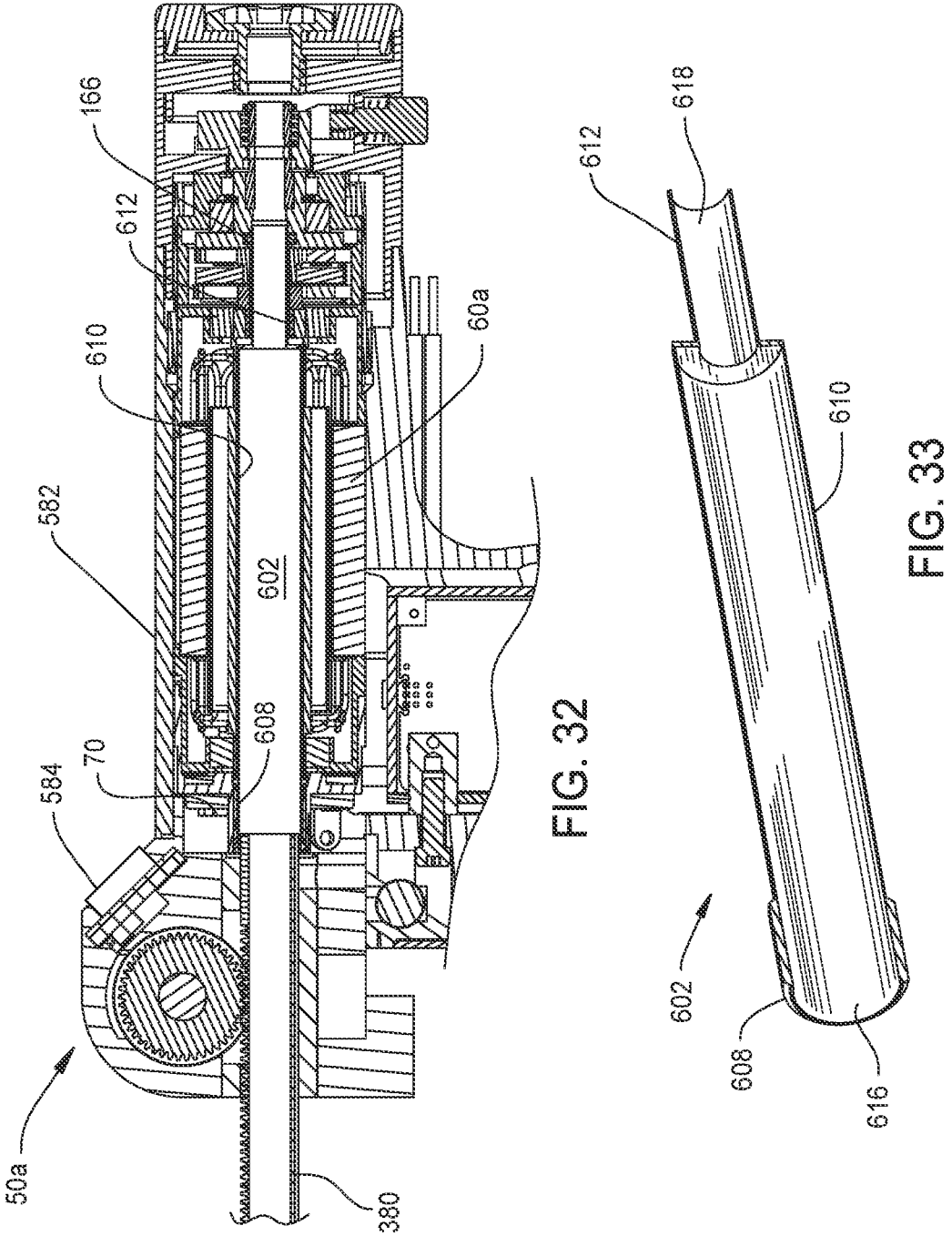
FIG. 32 is a cross sectional view of alternative drill of this invention.
FIG. 33 is a perspective and cross sectional view of the static cannula internal to the alternative drill of FIG. 32.

FIG. 32 depicts a portion of an alternative drill 50a of this invention. In FIG. 32 the drill bit is not shown disposed in the motor rotor. The drill 50a includes the housing 582 and display 584 described above.

Drill 50a also includes a motor 60a. Motor 60a is substantially identical to the first described motor 60. Motor 60a includes an additional component, a static cannula 602 seen best in FIG. 33. Static cannula 602 includes a tubular trunk 610. Trunk 610 has an outer diameter less than the diameter of the inner surface of rotor 110 that defines bore 117. At the proximal end of the trunk 610 a ring like head 608 protrudes radially outwardly and circumferentially around the trunk. The outer cylindrical surface of the head 608 is typically provided with threading (not illustrated). More particularly, the head 610 is shaped to seat in the bore 72 internal to the front cap boss 70. A tail 612, also tube like, extends proximally from the proximal end of the trunk 612. Stationary cannula 602 is formed so that the tail has an outer diameter less than that of the trunk 610. More particularly the outer diameter of tail 612 is such that the tail can seat in and be spaced inwardly from the surface internal to the boss 158 of carrier 156 that defines bore 162. The static cannula 602 is further formed so that the inner wall that defines the bore 618 that extends through tail 612 has a diameter sufficient to allow the drill bit 450 to seat and freely rotate in the tail.

Static cannula 602 has two contiguous bores that extend axially through the cannula. A bore 616 extends proximally from the distal end of the head 608, through the head and to the proximal end of the trunk 610. Bore 616 opens into a bore 618. Bore 618 extends through the tail 612 of the cannula 602 and forms the opening at the proximal end of the cannula. Bore 618 it should be understood has a diameter less than the diameter of bore 616.

When motor 60a is assembled, the stationary cannula 602 is inserted in the motor so the cannula trunk 610 seats in rotor bore 117. As a result of this seating of the cannula 602 in the rotor 110, the cannula tail extends through the bore 150 of carrier 148 and into bore 162 internal to boss 158. The O-ring 166 presses against the outer surface of cannula tail 612.

In this version of the invention, front cap 62 is formed so the inner surface of boss 70 that defines bore 72 is formed with threading (not illustrated). The stationary cannula 602 is fixedly secured in the rotor bore 117 by rotating the cannula 602 so the threading around the cannula head 608 engages the threading internal to boss 70.

Drill 50a is used in the same manner in which the first described drill 50 is used. The only appreciable difference in use is that when the drill bit 450 is fitted to drill 50a, the bit extends through bores 616 and 618 internal to the static cannula 602 prior to extending into the spindle 174.

A benefit of drill 50a is that the static cannula 602 functions as a barrier between the ambient environment and moving components of the motor 60a. This barrier prevents the fluids and debris that are present when the drill 50a is employed from contacting the moving components of the motor 60a.

The above is directed to one specific version of this invention. Other versions of this invention may have features different from what has been described.

For example, in alternative versions of this invention, the motor may be a pneumatic motor or a hydraulic motor.

Further, there is no requirement that in all versions of the invention, the probe that extends forward from the drill be a cannula that essentially circumferentially surrounds the drill bit. In alternative versions of the invention, the probe may be a rod that subtends a relatively small arc around the drill bit. Alternatively, the probe may consist of plural arcuately spaced apart rods. In these versions of the invention, a stop, that subtends a larger arc may be located at the distal end of the rod (or rods). A benefit of this version of the invention is that this type of probe provides an even smaller obstruction of the field of view of the site to which the drill bit 450 is applied than the cannula of the primary described version of the invention. Generally, it should be understood that in most versions of the invention, within at least the distalmost 10 mm section of the probe and more particularly within at least the distalmost 15 mm section of the probe, the inner surface of the probe, the surface adjacent the drill bit, is spaced no more than 2 mm from the drill bit. Within at least the distalmost 10 mm of the probe and more preferably within the distalmost 15 mm of the probe, the outer surface of the probe, the surface spaced furthest away from the drill bit, is located a maximum of 5 mm away from the drill bit.

Similarly, this invention is not limited to drills in which the transducer assembly that measures displacement of the drill relative to the probe includes a gear that engages the probe or a potentiometer that measures gear rotation. In alternative versions of the invention, a linear variable differential transformer may function as the transducer that measures the relative movement of the drill to the probe and provides a signal representative of this movement. The sensor signal will vary based on the relative location of the magnet to the sensor. Based on changes in this sensor signal, the signal processor is able to determine the movement of the drill relative to the probe.

In versions of the invention in which the cannula 380 is provided with teeth 382, the transducer may be a transducer that generates signals as a function of the transit of the teeth past the sensor. One such sensor is the ATS605LSG Dual Output Differential Speed And Direction Sensor available from Allegro MicroSystems of Worcester, Massachusetts. In this version of the invention, each time a tooth 382 passes by the transducer, the transducer outputs a distinct pulse signal. The number of pulses emitted by the transducer is representative of the number of teeth that move past the sensor. The number of teeth that move past the sensor is corresponds to the distance the drill 50 has advanced over the cannula 380.

Alternatively, the sensor may be an optical sensor. In these versions of the invention, the probe is formed with marking that are readable by the sensor. Other sensor capable of providing a signal representative of the movement of one components relative second component may also be employed.

It is further within the scope of the invention that some or substantially all of the components of the transducer assembly 260, including the display 410, be removably mounted to the drill housing 52. A benefit of these versions of the invention is that these removable components do not need to be designed to withstand the rigors of repeated sterilization processes. In some versions of the invention, the probe is built into the removable module that includes the transducer assembly. In still other versions of the invention the probe is removably attached to the drill housing.

In some versions of the invention, the elongated groove that extends laterally along the outer surface of the probe, groove 384 of cannula 380, may start at a location distal to the proximal end of the probe or terminate at a location proximal to the distal end of the probe. In these versions of the invention the abutment of the boss 325 against the end or ends of the groove limits the movement of the probe relative to the drill.

Likewise, it should be understood that the common opening in the drill housing 52 through which both the cannula 380 and drill bit 450 extend distally forward need not always be in the bushing that supports the cannula for the slidable movement. Similarly, this common opening may not always be an opening formed in a component that forms part of transducer assembly.

In regard to the bushing itself, the bushing may not always be the single piece assembly described with respect to the primary version of the invention. In some versions of the invention, the bushing may consist of two or more spaced apart members that hold the probe so as to allow longitudinal movement of the probe while inhibiting movement away from the axis of the drill bit 450. This flexure, if it were allowed to occur, could adversely affect the ability of the drill to provide an accurate measure of bore depth. A more serious effect of allowing this flexure is that it could result in the probe pressing against the rotating drill bit. Generally it is believed that to prohibit flexing of the probe, the bushing assembly should restrain the probe from lateral movement, side-to-side movement, along a distance that is at least 1 cm long, more often at least 1.5 cm in length and more preferably still at least 2 cm in length.

Similarly, other devices than the described spiral spring may be incorporated in the drill of this invention to provide the force that biases the probe distally forward. In some versions of this invention, this force may be provided by a spring that applies a longitudinal force directly on the probe. It is likewise within the scope of this invention that the assembly that provides this biasing force be one that relies on a magnetic or electromagnet force to urge the probe distally forward. It should thus be appreciated that it falls within the scope of this invention to provide a biasing member that urges the probe distally forward that is not integral with the transducer assembly. Thus, for example in a version of the invention in which the transducer assembly is different from the described transducer assembly, the biasing member that urges the probe distally forward may not be part of the transducer assembly. This if the transducer assembly is an optical sensor the biasing member may be a helical spring disposed in the rotor bore that pushes against a proximal portion of the probe.

There is no requirement that in all versions of the invention a gear train, sometimes referred to as a transmission, be present between the motor rotor and the coupling assembly that releasably holds the drill bit to the motor for rotation. In versions of the invention in which a gear train is present, the gear train may have a structure different from what has been described. Thus, it is within the scope of this invention that the gear train include a single planetary gear assembly or three or more planetary gear assemblies.

Further when the transmission is present, the transmission may not always physically be located between the motor 60 and the drive spindle 174, the component to which the drill bit 450 is coupled. In some versions of the invention the components may be arranged so that the drive spindle is located between the motor and the transmission.

Likewise, there is no requirement that in all versions of the invention in which the transmission is present that the transmission reduce the rotational speed of the drive spindle relative to the speed of the motor rotor. It is within the scope of this invention that the transmission may actually serve to increase the speed of rotation of the drive spindle relative to that of the motor. Similarly, in some versions of the invention, the transmission may only serve to transfer the rotational motion of the motor rotor to the drive spindle without causing either an increase or decrease in rotational speed of the drive spindle relative to the rotor.

Further this invention is not limited to a drill constructed so that the rotor that drives the drill bit and in which both the drill bit are seated is the rotor internal to the drill motor. An alternative drive of this invention may be one in which the motor rotor and drill bit-receiving rotor are separate from each other. Thus, an alternative drill of this invention may be constructed so that the motor is contained with the handgrip of the drill housing. The rotor that both rotates the drill bit and that receives the probe is rotatably contained with the barrel of the housing. In these versions of the invention, the motor has a rotor is disposed with the windings. A gear assembly transmits the rotational moment of this rotor to a second rotor. This second rotor is the rotor to which the drive spindle is connected. In some versions of the invention, this gear assembly also functions as the transmission that steps down the rotational moment so the rotor through which the drill bit and probe extend rotate at a speed slower than the rotational speed of the motor drive shaft. In still other variations of this version of the invention, the motor rotor and drill bit-receiving rotor turn at the same speed. A gear assembly similar to gear assembly similar to gear assembly 142 steps down the speed of the drive spindle, the component to which the drill bit 450 is actually coupled, so the drive spindle rotates at a speed less than the speed at which the rotor turns.

It should likewise be understood that, in some versions of the invention, the drill may not include a rotor with a bore through which the drill bit extends and in which the probe is slidably received. It falls within the scope of the drill of this invention to construct the drill so that motor is located proximal to the coupling assembly that connects the drill bit 450 for rotation by the motor. In still other versions of the invention, components other than a rotor may transfer torque from the output shaft of the motor to the spindle or other component to which the drill bit is removably connected. It should be understood that in these versions of the invention, it may not be necessary to include a rotor with a bore that transfers torque to the drill bit coupling assembly. In these versions of the invention, to reduce the extent to which the probe obstructs the view of the drill bit and adjacent tissue, the probe 380 extends distally forward from the handpiece through the opening through which the drill bit 450 extends. Again, in these versions of the invention, a bushing assembly is most likely present to prevent lateral movement of the probe.

It is further within the scope of this invention that the coupling assembly used to releasably hold the drill bit to the motor 60 be different from what has described. For example, one alternative coupling assembly that can be incorporated into the drill of this invention is a coupling assembly with a collet that has flexible feet. A collar that is selectively moveable holds the feet against the drill bit so as to place the coupling assembly in the locked state. Alternatively, by moving the collar the feet are able to flex away from the drill bit. This facilitates the removal of the drill bit and the loading of a new drill bit. The further understanding of this type of coupling assembly can be obtained from US Pat. Pub. No. 2002/0058958/PCT Pub. No. WO 2001/0060261 the contents of which are incorporated herein by reference.

In versions of the invention without a transmission assembly, the drive spindle may be integral with the motor rotor. Thus, in theses versions of the invention the coupling assembly essentially directly secures the drill bit 450 to the motor rotor 60 so the drill bit rotates in unison with the motor rotor.

It should be understood that there is no requirement that in all versions of the invention the housing be pistol shaped.

In the described version of the invention, processor 408 determines and displays the final value of the depth of the bore formed in the bone based on the surgeon's determining that the drill bit 450 has fully bored through the bone. In other versions of the invention, the input cue that triggers the final determination by the processor 408 of bore depth may be different from what has been described. Thus in some versions of the invention, the input cue that the drill bit 450 has broken through the bone may be based on one or more of the input variables: depth of bore; speed of advancement of drill bit through the bone, including changes in acceleration; torque output by the motor; current drawn by the motor; or motor speed. Similarly, the variables used to determine bore depth may include one or more above the listed variables.

Further there is no requirement that in all versions of the invention the display on which the data regarding bore depth is presented by built into the handpiece. In some versions of the invention, this display may be on a remote console. Thus, the display can be part of image presented on the remote console used to source power to the motor 60. Similarly, the processor that, in response to the signals output by the transducer assembly 260 determines the depth of the bore may likewise built into the remote console that includes the display. In these versions of the invention it is understood that a cable from the drill housing 52 to the console includes the conductors over which the signals from the transducer assembly 260 are forwarded to the processor.

Further the method of determining breakthrough of a bore of this invention described with respect to FIGS. 27A and 27B maybe practiced using assemblies for determining bore depth other than the assembly of this invention. Thus, this method can be used with an assembly that measures bore depth with a probe that is spaced more than 5 mm away from the drill bit. Alternatively, the sensor that measures depth of drill penetration be an assembly that, by monitoring the time it takes for waves to reflect back to the transducer assembly determine the advance of the drill to the bone and, by extension, the depth of drill bit penetration.

Further there may be variations in the process steps. For example the step 498 of determining breakthrough depth may only be determined once, after the comparison of step 504 indicates that the determined depth has returned to the zero depth.

Likewise, while the drill of this invention is generally described as a surgical drill, this use should not be considered limiting. Alternative drills of this invention can be used to simultaneously form bores in material other than living tissue and measure the depth of the formed bores. Thus depending of the type of the drill bit attached to the drill 50, the drill of this invention can be used to form a bore in material such as wood, metal, stone, concrete, cement or asphalt.

Accordingly, it is an object of the appended claims to cover all such variations and modifications that come within the true spirit and scope of this invention.

What is claimed is:

1. A surgical handpiece for actuating a drill bit and measuring a depth of a bore formed by the drill bit, said surgical handpiece comprising:
   a drill housing;
   a drill bit;
   a motor being operatively coupled to the drill bit and disposed in the drill housing such that rotation of a motor rotor results in rotation of the drill bit; and
   a transducer assembly mounted to the drill housing comprising:
      a probe being slidably mounted to the drill housing so as to extend forward from the drill housing and to retract into the drill housing, and the probe circumferentially surrounding the drill bit,
      a gear configured to rotate in response to extension and retraction of the probe, and
      a transducer configured to generate signals responsive to rotation of the gear that are representative of a distance the drill housing moves relative to a distal end of the probe when the drill bit is operatively coupled to the motor.

2. The surgical handpiece of claim 1, wherein the transducer assembly is removably mounted to the drill housing.

3. The surgical handpiece of claim 1, wherein the transducer comprises a potentiometer.

4. The surgical handpiece of claim 1, further comprising a biasing member that exerts torque on the gear to rotate the gear to engage the probe to urge the probe distally forward.

5. The surgical handpiece of claim 1, further comprising a bushing defining an opening for slidably receiving the probe while inhibiting lateral movement of the probe, and wherein the gear engages the probe between head and foot ends of the bushing while the probe is received in the opening of the bushing.

6. The surgical handpiece of claim 1, wherein the probe comprises a cannula having a tubular shape.

7. The surgical handpiece of claim 6, wherein the cannula defines a lumen along a length of the cannula, and wherein a distal end of the cannula is formed with a taper such that a wall thickness of the cannula at a distal-most end is less than a wall thickness of the cannula proximal to the distal-most end.

8. The surgical handpiece of claim 6, wherein the cannula comprises teeth spaced forward from a proximal end of the cannula for engaging the gear.

9. The surgical handpiece of claim 1, further comprising a display configured to present an indication of a depth of the bore formed by the drill bit when the drill bit is coupled to the motor.

10. The surgical handpiece of claim 9, wherein the display is removably mounted to the drill housing.

11. A transducer assembly configured to be coupled to a surgical handpiece having a housing surrounding a bit to measure a depth of a bore formed by the bit, said transducer assembly comprising:

a shell configured to be coupled to the housing of the surgical handpiece;

a probe being slidably mounted to the shell so as to extend forward from the shell and to retract into the shell;

a gear rotatably coupled to the shell and configured to rotate in response to extension and retraction of the probe;

a bushing defining an opening for slidably receiving the probe while inhibiting lateral movement of the probe; and a transducer configured to generate signals responsive to rotation of the gear that are representative of a distance the housing moves relative to a distal end of the probe when the bit is operatively coupled to the surgical handpiece and the shell is coupled to the housing;

wherein the gear engages the probe between head and foot ends of the bushing while the probe is received in the opening of the bushing.

12. The transducer assembly of claim 11, wherein the transducer comprises a potentiometer.

13. The transducer assembly of claim 11, further comprising a biasing member that exerts torque on the gear to rotate the gear to engage the probe to urge the probe distally forward.

14. The transducer assembly of claim 11, wherein the probe comprises a cannula having a tubular shape.

15. The transducer assembly of claim 14, wherein the cannula has a groove extending longitudinally.

16. The transducer assembly of claim 14, wherein the cannula comprises teeth spaced forward from a proximal end of the cannula for engaging the gear.

17. The transducer assembly of claim 16, wherein the teeth extend a distance greater than 30 percent of a length of the cannula.

18. The transducer assembly of claim 14, wherein the cannula defines a lumen along a length of the cannula, and wherein a distal end of the cannula is formed with a taper such that a wall thickness of the cannula at a distal-most end is less than a wall thickness of the cannula proximal to the distal-most end.

19. A transducer assembly configured to be coupled to a surgical handpiece having a housing surrounding a bit to measure a depth of a bore formed by the bit, said transducer assembly comprising:

a shell configured to be coupled to the housing of the surgical handpiece;

a probe being slidably mounted to the shell so as to extend forward from the shell and to retract into the shell;

a gear rotatably coupled to the shell and configured to rotate in response to extension and retraction of the probe; and a transducer configured to generate signals responsive to rotation of the gear that are representative of a distance the housing moves relative to a distal end of the probe when the bit is operatively coupled to the surgical handpiece and the shell is coupled to the housing;

wherein the probe comprises a cannula having a tubular shape and teeth spaced forward from a proximal end of the cannula for engaging the gear.

* * * * *